United States Patent
Song et al.

(10) Patent No.: US 11,965,844 B2
(45) Date of Patent: Apr. 23, 2024

(54) METHODS AND SYSTEMS FOR CHARACTERIZING A POROUS ROCK SAMPLE EMPLOYING COMBINED CAPILLARY PRESSURE AND NMR MEASUREMENTS

(71) Applicant: Schlumberger Technology Corporation, Sugar Land, TX (US)

(72) Inventors: Yi-Qiao Song, Newton Center, MA (US); Andre Souza, Rio de Janeiro (BR); Muthusamy Vembusubramanian, Acton, MA (US); Tuanfeng Zhang, Lexington, MA (US); Wenyue Xu, Medford, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 506 days.

(21) Appl. No.: 17/421,406

(22) PCT Filed: Jan. 8, 2019

(86) PCT No.: PCT/US2019/012593
§ 371 (c)(1),
(2) Date: Jul. 8, 2021

(87) PCT Pub. No.: WO2020/145942
PCT Pub. Date: Jul. 16, 2020

(65) Prior Publication Data
US 2022/0082517 A1   Mar. 17, 2022

(51) Int. Cl.
*G01N 24/08* (2006.01)
*G01N 33/24* (2006.01)

(52) U.S. Cl.
CPC ........... *G01N 24/081* (2013.01); *G01N 33/24* (2013.01)

(58) Field of Classification Search
CPC ............................ G01N 24/081; G01N 33/24
See application file for complete search history.

(56) References Cited

U.S. PATENT DOCUMENTS 5,069,065 A   12/1991   Sprunt et al.
6,462,542 B1  10/2002   Venkataramanan et al.
(Continued)

FOREIGN PATENT DOCUMENTS

| CN | 107727679 A | * | 2/2018 | ............ E21B 49/02 |
| WO | 2017100565 A1 | | 6/2017 | |
| WO | WO-2017100565 A1 | * | 6/2017 | ............ E21B 49/00 |

OTHER PUBLICATIONS

H. H. Yuan and B. F. Swanson, Resolving Pore-Space Characteristics by Rate-Controlled Porosimetry SPE Form. Eval. 5, 17 1989.
(Continued)

*Primary Examiner* — Michael J Dalbo
*Assistant Examiner* — Kaleria Knox
(74) *Attorney, Agent, or Firm* — Jeffrey D. Frantz

(57) ABSTRACT

A method (and corresponding system) that characterizes a porous rock sample is provided, which involves subjecting the porous rock sample to an applied experimental pressure where a first fluid that saturates the porous rock sample is displaced by a second fluid, and subsequently applying an NMR pulse sequence to the rock sample, detecting resulting NMR signals, and generating and storing NMR data representative of the detected NMR signals. The application of experimental pressure and NMR measurements can be repeated over varying applied experimental pressure to obtain NMR data associated with varying applied experimental pressure values. The NMR data can be processed using inversion to obtain a probability distribution function of capillary pressure values as a function of NMR property values. The probability distribution function of capillary (Continued)

pressure values as a function of NMR property values can be processed to determine at least one parameter indicative of the porous rock sample.

20 Claims, 21 Drawing Sheets

(56) References Cited

U.S. PATENT DOCUMENTS

| | | | |
|---|---|---|---|
| 7,352,179 B2* | 4/2008 | Chen | G01N 24/08 |
| | | | 324/303 |
| 9,052,409 B2 | 6/2015 | Prange et al. | |
| 9,551,769 B2* | 1/2017 | Fordham | G01R 33/50 |
| 2008/0303520 A1* | 12/2008 | Chen | G01R 33/44 |
| | | | 324/309 |

OTHER PUBLICATIONS

Song et al. T1-T2 Correlation Spectra Obtained Using a Fast Two-Dimensional Laplace Inversion, in Journal of Magnetic Resonance 2002, vol. 154, pp. 261-268.
Song, Venkataramanan, Kausik, Heaton, Two-Dimensional NMR of Diffusion and Relaxation, a chapter in Diffusion NMR of Confined Systems: Fluid Transport in Porous Solids and Heterogeneous Materials, edited by Rustem Valiullin, Royal Society of Chemistry, 2016, 51 pages.
S. W. Provencher. Contin: A general purpose constrained regularization program for inverting noisy linear algebraic and integral equations. Comput. Phys. Commun., 1982, 27: 229-242.
Kenyon, "Petrophysical Principles of Applications of NMR Logging," Log Analyst, vol. 38(2), 1997, (23 pages).

Xiong, Baychev, Jivkov, Review of pore network modelling of porous media: Experimental characterisations, network constructions and applications to reactive transport, Journal of Contaminant Hydrology 192 (2016) 101-117.
Dong H (2007) Micro-CT imaging and pore network extraction, PhD OR doctoral dissertation, Imperial College London, UK, (213 pages).
Curtis M, Ambrose R, Songdergeld C, Rai C (2010) Structural characterization of gas shales on the micro- and nano-scales, SPE 137693, (15 pages).
Fredrich J (1999) 3D imaging of porous media using laser scanning confocal microscopy with application to microscale transport processes. Phys Chem Earth (A) 24: 551-561.
Sok R, Knackstedt M, Sheppard A, Pinczewski W, Lindquist W, Venkatarangan A, Paterson L (2002) Direct and stochastic generation of network models from tomographic images; effect of topology on residual saturations. Transport in Porous Media 46: 345-371.
Blunt M, Jackson M, Piri M, Valvatne P (2002) Detailed physics, predictive capabilities and macroscopic consequences for porenetwork models of multiphase flow. Advances in Water Resources 25: 1069-1089.
Zhang, "MPS-Driven digital rock modeling and upscaling", Math Geosci, vol. 47, 2015, pp. 937-954.
Hassler, G. L., Brunner, E., "Measurement of Capillary Pressure in Small Core Samples", Trans. AIME, 1945, 160, 114-123.
N. T. Burdine, Relative Permeability Calculations from Pore Size Distribution Data, Petroleum Trans. AIME 198, 71 (1953) (8 pages).
Zhi-Xiang Luo, Jeffrey L Paulsen, and Yi-Qiao Song, "Robust determination of surface relaxivity from nuclear magnetic resonance DT2 measurements," Journal of Magnetic Resonance, vol. 259, 2015, pp. 146-152.
International Search Report and Written Opinion issued in PCT Application PCT/US2019/012593 dated Oct. 7, 2019 (9 pages).
International Preliminary Report on Patentability issued in PCT Application PCT/US2019/012593 dated Jul. 22, 2021, 6 pages.

* cited by examiner

METHODS AND SYSTEMS FOR CHARACTERIZING A POROUS ROCK SAMPLE EMPLOYING COMBINED CAPILLARY PRESSURE AND NMR MEASUREMENTS

CROSS-REFERENCE TO RELATED APPLICATIONS

This application is a National Stage Entry of International Application No. PCT/US2019/012593, filed Jan. 8, 2019.

FIELD

The present disclosure relates to characterizing porous rock samples. More specifically, it relates to characterizing fluid properties and rock properties of a porous rock sample.

BACKGROUND

In a porous rock, pores are typically connected to form a continuous pore space. Fluids (such as water or oil) may flow through the pores when driven by pressure. The fluid often flows through large pores and then smaller pores and the flow properties are sensitive to the pore sizes. For example, the pores can be modelled as cylindrical capillary tubes and the flow rate through a given tube can be determined by the diameter of the flow channel and the fluid viscosity. In standard fluid-dynamics notation, $$\Delta P = \frac{8\mu L Q}{\pi R^4}, \quad \text{Eqn. (1)}$$

where $\Delta P$ is the pressure difference between the two ends,
L is the length of the tube,
$\mu$ is the dynamic viscosity,
Q is the volumetric flow rate, and
R is the radius of the tube.

This equation can be used to obtain flow rate if the pressure difference is known. One can see that a smaller tube will reduce the flow rate sharply from the $1/R^4$ relationship. If a flow trajectory passes through both smaller pores and larger pores, the smallest pore often determines the ultimate flow rate. In this example, the smallest pore in the flow path is often called pore throat while the larger pores the pore body. Thus, it is important to understand how large pores are connected to small pores in order to predict the flow rate, or the permeability of the rock formation.

In another example, the porous nature of a rock sample can be described by a pore network model that includes variable size pore bodies with variable size pore throats that connect adjacent pairs of pore bodies. The size of a pore body characterizes local volumetric capacity of the pore network. The size of a pore throat characterizes the cross-sectional area of flow between adjacent pores. The pore network can have many configurations. For example, it is possible that a subnetwork of larger pore bodies and pore throats are spatially separated from a subnetwork of smaller pore bodies and pore throats. In this case, when the rock is subject to a pressure differential, the larger pore sub-network will dominate the flow rate and the smaller pore sub-network will essentially not flow. In another example, larger pore bodies can always be connected to other larger pore bodies through smaller pore bodies and pore throats. For example, the larger pore bodies can always be surrounded by smaller pore bodies and probe throats. In this case, the smaller pore network will dominate the flow rate and thus the flow permeability can be very low.

NMR relaxation measurements (such as T1 and T2) are commonly used to detect pore size distribution that characterizes local volumetric capacity of the pore space of a rock sample. However, such NMR relaxation measurements do not distinguish between pore body and pore throat and thus cannot distinguish the different types of pore elements.

Capillary pressure measurements are commonly used to characterize pore throat size of reservoir rock. However, such capillary measurements do not provide information that describes both pore body and pore throat.

Capillary pressure $P_c$ is a property of the porous rock sample and can be defined as the pressure differential between two immiscible fluid phases occupying the pore space of the rock which is caused by interfacial tension between the two phases and which must be overcome to initiate flow. The wettability of the porous reservoir rock is an important factor in the capillary pressure relationships. Wettability describes the preference of the porous reservoir rock to be in contact with one fluid rather than another and thus describes the balance of surface and interfacial forces. For an oil-water system, a "strongly water-wetting" reservoir rock describes one end of a wettability continuum in which the reservoir rock strongly prefers contact with water, while a "strongly oil-wetting" reservoir rock describes the opposite end of the wettability continuum in which the reservoir rock prefers contact with oil. Other degrees of wettability apply along this continuum.

The capillary pressure of a reservoir rock sample is often characterized by well-known mercury intrusion, porous plate, or centrifuge methods. The mercury intrusion method is rapid, but it is destructive, and the mercury/vacuum system may not accurately represent the wettability of reservoir system. The porous plate method is a direct and accurate technique, but is extremely time-consuming, since the equilibrium time can range from a week to months per pressure point.

The centrifugal method was introduced by Hassler and Brunner in 1945, as described in Hassler, G. L., Brunner, E., "Measurement of Capillary Pressure in Small Core Samples", Trans. AIME, 1945, 160, 114-123 and N. T. Burdine, Trans. AIME 198, 71 (1953). This technique, which involves rotating a fluid bearing rock core at variable speeds in a specially modified centrifuge, has been extensively investigated, and is commonly used in the petroleum industry. The sample rotation yields a centrifugal force which will empty the pores of the sample with matching capillary forces. Collecting the expelled fluid as a function of increasing rotational speed permits a quantification of the capillary pressure as a function of fluid content or saturation. The centrifuge method is advantageous because it employs a shorter equilibrium and experimental time and can use reservoir fluids. However, it requires special instrumentation, including a stroboscope for measuring the expelled liquid.

As part of the centrifugal method, the rock sample is typically saturated completely with a wetting fluid (e.g., water), and then placed in a centrifuge and rotated at progressively higher speeds. The speed of rotation generates a centrifugal force that displaces the wetting fluid from the rock sample replacing it with the non-wetting fluid loaded into the sample holder. At slow rotation speeds, the force is sufficient to displace water from the largest pores. At higher speeds, the force displaces the wetting fluid from smaller and smaller pores in the sample. The result is a capillary pressure curve that describes the capillary pressure $P_c$ of the rock sample as a function of the fluid saturation. An example plot that illustrates an exemplary capillary pressure curve is shown in FIG. 1.

Pore throat size of a rock sample can be related to capillary pressure $P_c$ by the following:

$$P_c = \frac{2\gamma \cos\theta}{R}, \qquad \text{Eqn. (2)}$$

where $\gamma$ is the interfacial tension;
R is the effective radius of the capillary tube, and
$\theta$ is the wetting angle of the liquid on the surface of the capillary tube.

It indicates that the non-wetting fluid can enter the pore space of the sample only when the fluid pressure is higher than the capillary pressure $P_c$. Thus, the capillary pressure $P_c$ is also called entry pressure.

Taking the logarithmic function on both sides of Eqn. (2), one can obtain:

$$\log(P_c) = \log(2\gamma \cos\theta) - \log(R)). \qquad \text{Eqn. (3)}$$

Then, on a log-log plot of $P_c$ and R, the curve should be a line with slope of −1.

The capillary pressure $P_c$ of the rock sample at partial fluid saturation can also be measured by other known methods, such as porous plate method or multi-phase flow method.

However, these conventional capillary pressure measurements only determine the pore throat size and cannot characterize the size of the pore bodies of the pore space of the rock sample.

Previous work using Mercury intrusion experiments to obtain pore throat and pore body relationships have been reported. For example, the work of H. H. Yuan and B. F. Swanson, SPE Form. Eval. 5, 17 1989 is based on constant rate mercury injection (CRMI) method. CRMI is different from the conventional mercury injection in that it maintains a constant injection rate and monitors the fluctuations of the injection pressure. The injection rate is kept extremely low so that the pressure loss due to the flow inside the sample is negligible compared to the capillary pressure. The observation of a sudden pressure drop, referred to as "rheon," is a result of the movement of a single mercury meniscus from a narrow pore throat region into a wide pore throat region, accompanied by a simultaneous mercury redistribution within the pore space. The main limitation of this technique is that the injection rate must be very low to avoid pressure drop inside the sample and as a result, it is very difficult to perform on low permeability rocks.

High-resolution x-ray tomography can be used to image small rock samples (~1 mm cube) to 1-micron resolution. Such images can be used to identify pore body and the connecting pore throat. However, two weaknesses of this method are that the resolution may not be sufficient to capture all pores (smaller than the resolution), and the largest sample to be imaged is only 1-2 mm in length. It is very difficult to image larger samples that can be used for experimental validation and capture the full heterogeneity of a rock formation.

SUMMARY

A method (and corresponding system) that characterizes a porous rock sample is provided, which involves subjecting the porous rock sample to an applied experimental pressure where a first fluid that saturates the porous rock sample is displaced by a second fluid, and subsequent thereto, applying an NMR pulse sequence to the porous rock sample, detecting resulting NMR signals from the porous rock sample, and generating and storing NMR data representative of the detected resulting NMR signals. The application of experimental pressure and NMR measurements can be repeated over varying applied experimental pressure to obtain NMR data associated with varying applied experimental pressure values. The NMR data associated with varying applied experimental pressures can be processed using inversion to obtain a probability distribution function of capillary pressure values as a function of NMR property values. The probability distribution function of capillary pressure values as a function of NMR property values can be processed to determine at least one parameter indicative of the porous rock sample.

The NMR property values can be related to transverse relaxation time (T2) of hydrogen protons, which is often obtained by a CPMG pulse sequence. Other pulse sequences can also be used to obtain values for other NMR properties of the rock sample, such as inversion recovery sequence to obtain longitudinal relaxation time (T1) values, pulsed field gradient experiment to obtain diffusion coefficient (D) values. Several other multi-dimensional experiments have also been used extensively in petroleum sciences to characterize two dimensional maps of NMR property values of the rock sample, such as inversion-recovery-CPMG experiment for a T1-T2 map, and a diffusion editing-CPMG experiment for a D-T2 map. These methods can all be performed at different capillary pressures to obtain a range of NMR properties of the rock sample.

In embodiments, the at least one parameter indicative of the porous rock sample can include at least one frequency (or count) distribution of capillary pressure values for a specific pore size (and possibly a plurality of frequency distributions of capillary pressure values for different specific pore sizes).

In embodiments, the at least one parameter indicative of the porous rock sample can include a parameter indicative of bound fluid volume in the porous rock sample.

In embodiments, the parameter indicative of bound fluid volume in the porous rock sample can be derived by integration or addition along the dimensions of both the transverse relaxation values and the capillary pressure values.

In embodiments, the parameter indicative of bound fluid volume in the porous rock sample is Liven as BFV and can be calculated as $$BFV = \frac{1}{A} \int_{T2min}^{T2max} dT_2 \int_{P_c=P_{c-cut}}^{P_c=P_{c-max}} f(P_c, T_2) dP_c,$$

where A is the normalization parameter defined as $$A = \int_{T2min}^{T2max} dT_2 \int_{P_{c-min}}^{P_{c-max}} f(P_c, T_2) dP_c,$$

where $f(P_c, T_2)$ is the probability distribution function of capillary pressure values as a function of transverse relaxation values, Pc represents the dimension of the capillary pressure values, Pc-max represents a maximum capillary pressure value, Pc-min represents a minimum capillary pressure value, Pc-cut represents a capillary pressure value at which fluid is considered bound, $T_2$ represents the dimension of the transverse relaxation values, T2max represents a maximum $T_2$ value, and T2min represents a minimum $T_2$ value.

In embodiments, the at least one parameter indicative of the porous rock sample can include a parameter indicative of free fluid volume in the porous rock sample.

In embodiments, the parameter indicative of free fluid volume in the porous rock sample can be derived by integration or addition along the dimensions of both the transverse relaxation values and the capillary pressure values.

In embodiments, the parameter indicative of free fluid volume in the porous rock sample is given as FFV and can be calculated as $$FFV = \frac{1}{A}\int_{T2min}^{T2max} dT_2 \int_{P_c=Pc-min}^{P_c=Pc-cut} f(P_c, T_2)dP_c,$$

where A is the normalization parameter defined as $$A=\int_{T2min}^{T2max}dT_2\int_{Pc\ min}^{Pc\ max}f(P_c,T_2)dP_c,$$

where $f(P_c,T_2)$ is the probability distribution function of capillary pressure values as a function of transverse relaxation values, Pc represents the dimension of the capillary pressure values, Pc-max represents a maximum capillary pressure value, Pc-min represents a minimum capillary pressure value, Pc-cut represents a capillary pressure value at which fluid is considered bound, $T_2$ represents the dimension of the transverse relaxation values, T2max represents a maximum $T_2$ value, and T2min represents a minimum $T_2$ value.

In embodiments, at least one parameter indicative of the porous rock sample includes a parameter indicative of permeability of the porous rock sample.

In embodiments, the parameter indicative of permeability of the porous rock sample is given as k and can be calculated as $$k = c\Phi^4\left(\frac{FFV}{BFV}\right)^2$$

wherein c is a calibration constant, $\Phi$ is porosity of the porous rock sample, FFV is a parameter indicative of free fluid volume in the porous rock sample, and BFV is a parameter indicative of bound fluid volume in the porous rock sample.

In embodiments, the parameter indicative of permeability of the porous rock sample is given as $k_{SDR}$ and can be calculated as $$k_{SDR}=c\Phi^4 T_{2lm}^2,$$

wherein c is a calibration constant, $\Phi$ is porosity of the porous rock sample, and $T_{2lm}$ is a log mean of the frequency distribution of transverse relaxation values.

In embodiments, $T_{2lm}$ can be calculated from a free fluid distribution, which is determined from integration or addition of the probability distribution function of capillary pressure values as a function of transverse relaxation values of the form $$f_{FF}(T_2) = \frac{1}{A}\int_{P_c=Pc-min}^{P_c=Pc-cut} f(P_c, T_2)dP_c.$$

where A is the normalization parameter defined as $$A=\int_{T2min}^{T2max}dT_2\int_{Pc\ min}^{Pc\ max}f(P_c,T_2)dP_c,$$

where $f(P_c,T_2)$ is the probability distribution function of capillary pressure values as a function of transverse relaxation values, Pc represents the dimension of the capillary pressure values, Pc-max represents a maximum capillary pressure value, Pc-min represents a minimum capillary pressure value, Pc-cut represents a capillary pressure value at which fluid is considered bound, $T_2$ represents the dimension of the transverse relaxation values, T2max represents a maximum $T_2$ value, and T2min represents a minimum $T_2$ value.

In embodiments, the method (and system) can be configured to generate a pore network model of the porous rock sample based on the probability distribution function of capillary pressure values as a function of NMR property values.

In embodiments, the pore network model can include a frequency (or count) distribution of pore body diameters that are determined using the probability distribution function of capillary pressure values as a function of transverse relaxation values. The pore network model can include a frequency (or count) distribution of pore throat sizes that are determined using the probability distribution function of capillary pressure values as a function of transverse relaxation values.

In embodiments, the probability distribution function of capillary pressure values as a function of transverse relaxation values can be derived from inversion of the NMR data written in a two-dimensional matrix form.

In embodiments, the inversion of the NMR data involves an equation written in a two-dimensional matrix form as $$M=K1\cdot F\cdot K2^T,$$

where M is a two-dimensional matrix whose rows correspond to the number of echoes in the detected resulting NMR signals and whose columns corresponds to different applied experimental pressure values, F is a two-dimensional matrix whose rows correspond to different transverse relaxation values and whose columns corresponds to different capillary pressure values, K1 is a two-dimensional kernel matrix where element (i,j) of K1 is defined to be $$K1_{ij} = \exp\left[-\frac{t_i}{T_{2,j}}\right],$$

where $t_i$ is the i-th value of the echo time t for the echoes over the j transverse relaxation values of the F matrix; and K2 is a two-dimensional kernel matrix defined as:

$$K2_{kl}=S_w(P_{cent,k},P_{c,l}),$$

where $S_w(P_{cent,k},P_{c,l})$ is a step function or modified step function representing saturation of the pore sample as a function of applied experimental pressure.

In embodiments, the probability distribution function of capillary pressure values as a function of transverse relaxation values can be derived from inversion of the NMR data written in a one-dimensional matrix form.

In embodiments, the inversion of the NMR data involves an equation written in a one-dimensional matrix form as $$m = k \cdot f,$$

where m is a one-dimensional matrix whose i-th element corresponds to the data acquired with the i-th pair of echo time and applied experimental pressure, f is a one-dimensional matrix whose j-th element corresponds to the j-th pair of transverse relaxation value and capillary pressure value, k is a one-dimensional kernel matrix defined as $$k_{ij} = S_w(P_{cent,k}, P_{c,l}) \exp\left[-\frac{t_i}{T_{2,j}}\right]$$

where $S_w(P_{cent,k}, P_{c,l})$ is a step function or modified step function representing saturation of the pore sample as a function of applied experimental pressure, and $t_i$ is the i-th value of the echo time $t_{echo}$ for the echoes over the j transverse relaxation values of the f matrix.

In embodiments, the probability distribution function of capillary pressure values as a function of transverse relaxation values can be derived from inversion of the NMR data for each given capillary pressure values to obtain a distribution of transverse relaxation values for each given capillary pressure value.

In embodiments, the inversion of the distribution of transverse relaxation values for each given capillary pressure values involves an equation written in a two-dimensional matrix form as $$D = K_D \cdot F,$$

where D is a two-dimensional matrix whose rows correspond to the different transverse relaxation values and whose columns correspond to different applied experimental pressure values, F is a two-dimensional matrix whose rows correspond to different transverse relaxation values and whose columns corresponds to different capillary pressure values, and $K_D$ is a two-dimensional kernel matrix defined as $$K_{D,ij} = S_w(P_{cent,i}, P_{c,j})$$

where $S_w(P_{cent,k}, P_{c,l})$ is a step function or modified step function representing saturation of the pore sample as a function of applied experimental pressure.

In embodiments, the first fluid is a wetting fluid (for example, water), and the second fluid comprises a non-wetting fluid (for example, an oil or oil component such as decane).

In embodiments, a rotating centrifuge apparatus is configured to subject the porous rock sample to a desired applied experimental pressure.

In embodiments, a continuous-flow apparatus is configured to subject the porous rock sample to a desired applied experimental pressure.

In embodiments, the porous rock sample is a cylindrical core rock sample or cuttings. The cylindrical core rock sample can be 20 mm in diameter and 40 mm long (typical Hassler size), or 40 mm in diameter and a standard size length for core measurements. The cuttings can be pieces of a few mm in maximal dimension with irregular shapes or crushed rock powder (typically 1 mm size or smaller).

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Figure 2:
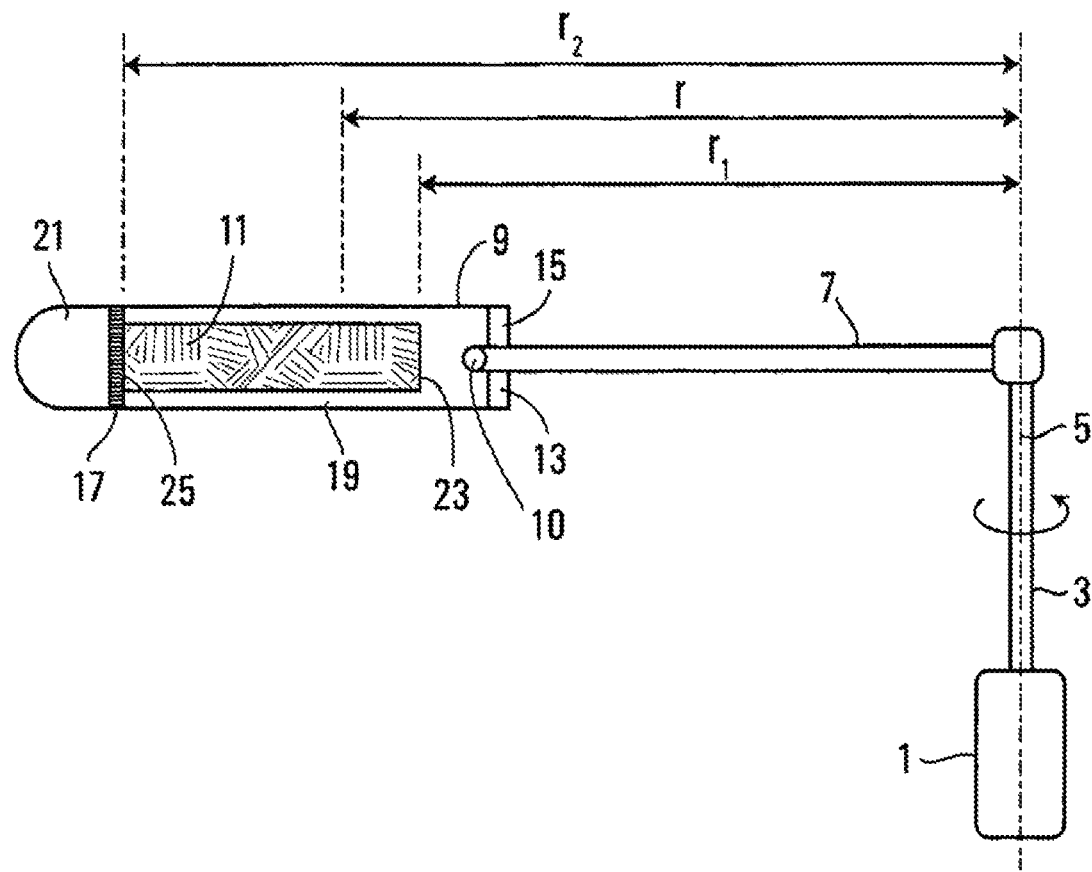
FIG. 2 is a schematic side view of an exemplary rotary centrifuge apparatus.

FIG. 2 shows a schematic diagram of a rotary centrifuge for use in spinning a porous rock sample as part a capillary pressure measurement, and which may be used in apparatus and methods of embodiments of the invention. The rotary centrifuge comprises a motor 1 which drives rotation of a shaft 3 about a rotational axis 5, an arm 7 rigidly connected to the shaft 3 and extending radially from the shaft 3, and a sample holder 9 releasably connected to the arm 7 about a connection point 10 at the end 15 of the arm 7. In this configuration, the motor 1 drives rotation of the sample holder 9 about the rotational axis 5 at a fixed offset from the axis 5. The sample holder 9 includes a removable sealed end part or closure 13 at the inner end 15 and a porous plate 17 which divides the interior space of the sample holder 9 into a first chamber 19 for containing a porous rock sample 11 and a second chamber 21 at the distal end thereof for collecting liquid 22 expelled from the sample through the porous plate 17.

The rock sample 11 can be a cylindrical core having an inlet face 23 spaced at a distance r1 from the rotational axis 5 and an outlet face 25 disposed adjacent the porous plate 17 and spaced at a distance r2 from the rotational axis 5. The distance represents the radial distance of any point in the sample from the rotational axis 5.

In centrifuge operations, the rock sample 11 is saturated with a wetting fluid (such as water) and confined in the interior space of the sample holder 9. The interior space of the sample holder 9 also contains a non-wetting fluid, which can replace the wetting fluid displaced from the rock sample when the sample holder 9 rotates about the axis 5 by operation of the motor 1. In one embodiment, the non-wetting fluid can be air or an oil or oil component such as decane, mineral oil, or crude oil.

When the cylindrical core rock sample 11 of length L is subjected to acceleration governed by angular velocity ω of the shaft 3 under operation of the motor 1, an experimental capillary pressure $P_{cent}$ is applied to the rock sample 11 which is given by:

$$P_{cent} = 2hd\omega^2(\rho_w - \rho_{nw}),\qquad\text{Eqn. (4)}$$

where h is the length of rock sample, ω is the angular velocity of the rotation of the rock sample, d is the distance (or r value) between the center of the rock sample 11 and the rotation axis 5, and $\rho_w$ and $\rho_{nw}$ are the density of the wetting and non-wetting fluids, respectively, that are used in the experiment.

The porous media of the rock sample 11 can be described as a collection of capillaries of a range of radius R. As the radius R becomes smaller, the capillary pressure increases according to Eqns. (2) and (3) above. For example, consider a rock sample with a broad pore size distribution. When the rock sample is subject to the centrifuge operations at a certain applied experimental capillary pressure $P_{cent}$, the fluid in pores with capillary pressure lower than $P_{cent}$ will be drained. Such a sample is called partially saturated. The pores that are smaller with higher capillary pressures than $P_{cent}$ will remain saturated. As the angular velocity is increased resulting in an increase in $P_{cent}$, the loss of fluid is from pores with $P_c < P_{cent}$. The saturation of the pore space of the rock sample 11 that result from the increasing of applied experimental capillary pressure $P_{cent}$ can be characterized by NMR measurements or experiments.

Figure 3:
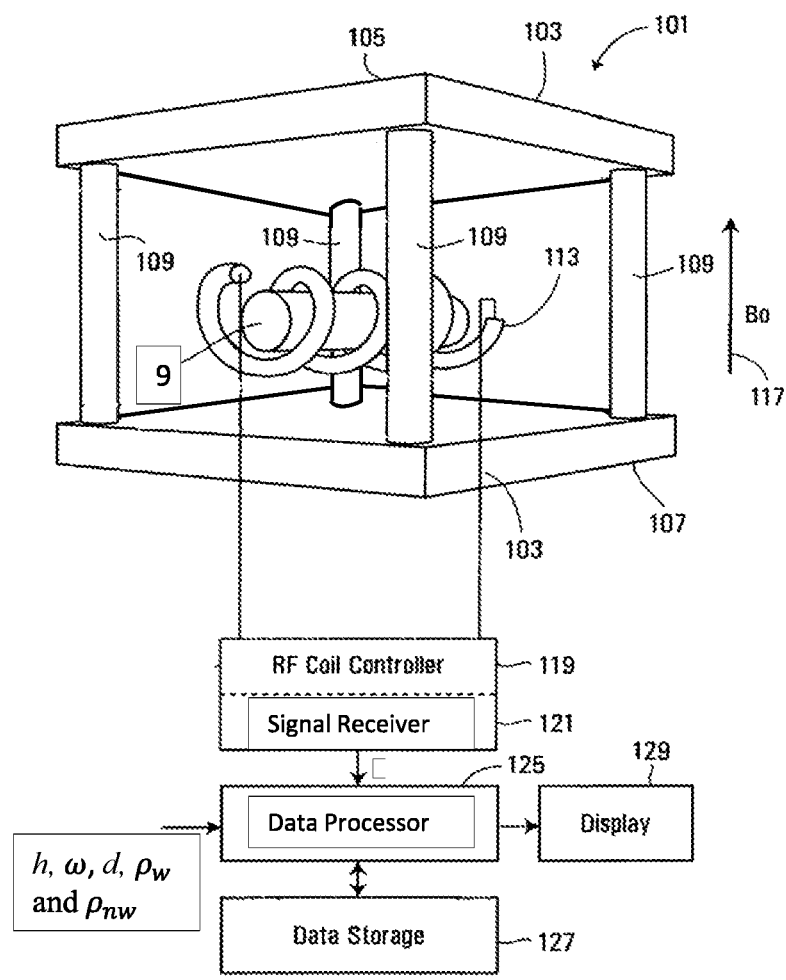
FIG. 3 is a schematic diagram of an exemplary nuclear magnetic resonance (NMR) system.

FIG. 3 shows a schematic diagram of an exemplary NMR system 101 that can be configured to conduct such NMR measurements. The NMR system 101 includes a permanent magnet having spaced apart magnetic pole pieces 105, 107, spacers (e.g., pillars) 109 separating the magnetic pole pieces 105, 107, and an RF coil 113 which is configured to receive the sample holder 9 and surround the rock sample contained therein. The arrow 117 shows the direction of the magnetic field, B0. Connectors 103 provide for electrical connection of the RF coil 113 to control circuitry as described below.

The NMR system 101 further includes an RF coil controller 119 for generating and delivering RF excitation pulses to the RF coil 113 for transmission into the space occupied by the rock sample as part of such NMR measurements, and a signal receiver 121 for receiving an NMR signal detected by the RF coil 113 as part of such NMR measurements. The NMR system 101 further includes a data processor 125 for receiving data from the signal receiver 121, data storage (memory) 127, and an optional display 129. The signal receiver 121 generates a signal or data which represents the NMR signal detected by the RF coil 113 and supplies such signal to the data processor 125 for processing.

Figure 4:
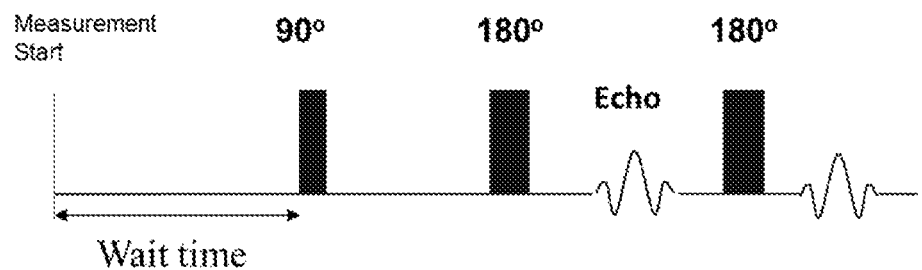
FIG. 4 is a schematic diagram of a CPMG pulse sequence that can be used by the NMR system of FIG. 3 to perform NMR relaxation experiments as part of the workflow described in the present disclosure.

The NMR measurements can use specially designed data acquisition schemes (called NMR pulse sequences) which describe the timings of transmission and reception of electromagnetic signals. The NMR pulse sequence for the measurement of a transverse relaxation time ($T_2$) frequency distribution is called the CPMG echo train and is shown in FIG. 4. The CPMG echo train consists of an initial idle time or wait time to allow the nuclei in the fluids contained in the rock sample to come to equilibrium with the magnetic field induced by the permanent magnet of the NMR system. Thereafter, a series of radio-frequency pulses are applied to the space occupied by the rock sample using the RF coil 113. The time between the adjacent 180-degree RF pulses is the echo spacing, TE. The initial wait time is often long enough to fully polarize the system. Midway between the 180-degree RF pulses, NMR signals called echoes are detected by the RF coil 113. The amplitude of the echoes decay or attenuate with time. The data processor 125 can be configured to obtain a $T_2$ frequency distribution by fitting the echo amplitudes to a multi-exponential model as follows.

In such an experiment, a train of echo signal is acquired. The signal amplitude, S, is measured as a function of the echo time, $t_{echo}$, which is the time of the echo from the beginning of the first 90-degree pulse and given by:

$$t_{echo} = n*TE, \qquad \text{Eqn. (5)}$$

where n is the number of echo, and TE is the echo spacing or time between two adjacent 180-degree pulses.

The signal amplitude $S(t_{echo})$ at a given echo time $t_{echo}$ then follows an exponential decay form given by:

$$S(t_{echo}) = S(0)\exp\left(-\eta * \frac{TE}{T_2}\right), \qquad \text{Eqn. (6)}$$

for a rock sample with a single $T_2$ component.

For many rock samples where a number of different $T_2$ components are present, the signal amplitude $S(t_{echo})$ at a given echo time $t_{echo}$ is a sum of all $T_2$ components, which is given by an integral over a range of T2 values as follows:

$$S(t_{echo}) = \int dT_2 f(T_2)\exp\left(-n * \frac{TE}{T_2}\right), \qquad \text{Eqn. (7)}$$

where $f(T_2)$ is the $T_2$ frequency distribution function.

It has been shown that the diffusional relaxation rate $T_2$ is directly proportional to the surface-to-volume ratio of the rock sample (and thus inversely proportional to pore size radius) as follows:

$$1/T_2 = \rho \cdot S/V_p, \qquad \text{Eqn. (8)}$$

where S is the total surface area of the material, $V_p$ is the pore volume, and $\rho$ is the surface relaxivity, which is a quantity (in micron/second) that defines the strength of the surface relaxation phenomenon. Typically, the surface relaxivity $\rho$ can be given as 3 um/s for sandstones or 1 um/s for carbonate rocks. Also, measurement of the surface relaxivity $\rho$ can be made on rock samples, such as by the method described by Zhi-Xiang Luo, Jeffrey L Paulsen, and Yi-Qiao Song, "Robust determination of surface relaxivity from nuclear magnetic resonance DT2 measurements," Journal of Magnetic Resonance, Vol. 259, 2015, pgs. 146-152. For a tube-shaped pore of diameter d, Eqn. (8) can be rewritten as $1/T_2 = 4\rho/d$.

Because of this relationship, NMR measurements of $T_2$ frequency distributions (and other parameters such as $T_1$ frequency distributions and diffusion coefficient D frequency distributions) are used extensively in petroleum exploration to obtain estimates of porosity, pore size, bound fluids, permeability, and other rock and fluid properties.

Figure 5A:
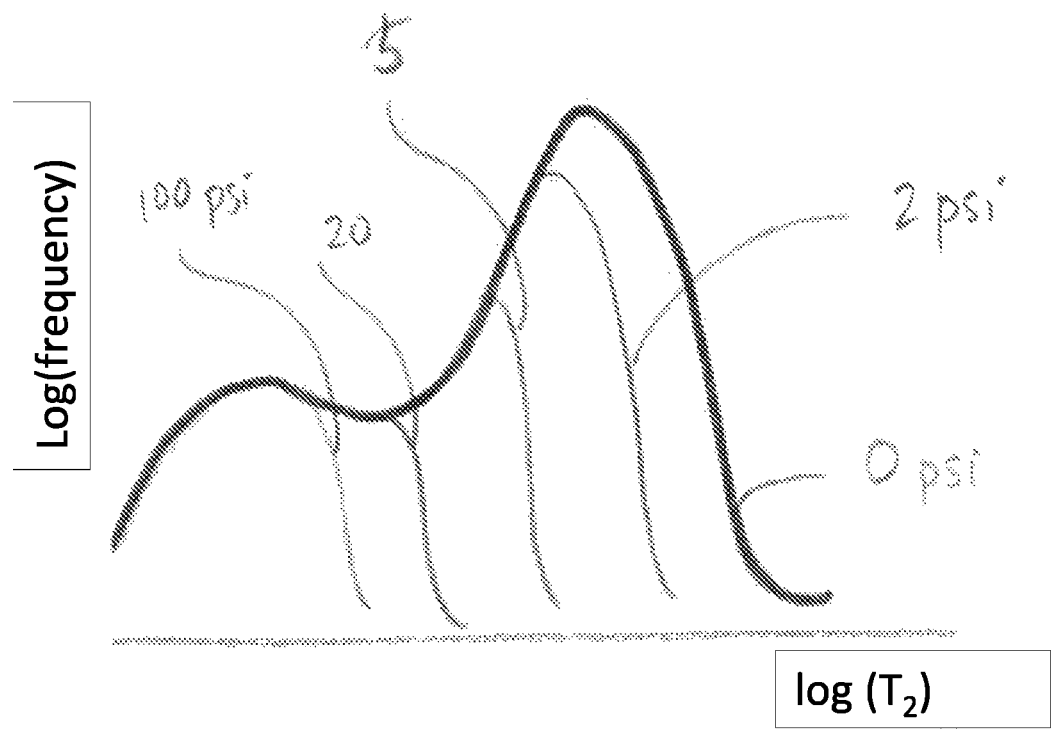
FIG. 5A is plot of $T_2$ frequency distributions of the porous rock sample as a function of applied experimental capillary pressure $P_{cent}$ obtained from NMR measurements of the rock sample performed over several iterations of increasing applied experimental capillary by operation of a rotary centrifuge apparatus (FIG. 1)

In the present disclosure, NMR measurement of $T_2$ frequency distribution can be combined with the centrifuge operations over a number of iterations of increasing applied experimental capillary pressure $P_{cent}$ to obtain data that represents the frequency distribution of $T_2$ values of the porous rock sample as a function of applied experimental capillary pressure $P_{cent}$. An example of such data is shown in the plot of FIG. 5A where the dimension of the X-axis is $\log(T_2)$ and the dimension of the Y-axis is log(frequency). Because pore size is inversely proportional to $T_2$ (as dictated by Eqn. (8)), the data allows for comparison of the pore size of the still saturated pores and that of the fully saturated sample as the applied experimental capillary pressure increases. In FIG. 5A, the curve labeled "0 psi" is the measured $T_2$ frequency distribution function for the case where $P_{cent}=0$ and corresponds to the fully saturated sample (before centrifuging). The curves labeled "2 psi," "5 psi," "20 psi," and "100 psi" are the measured $T_2$ frequency distribution functions for the iterations of increasing applied experimental capillary pressure $P_{cent}$ at values of 2 psi, 5 psi, 20 psi, and 100 psi, respectively. The data clearly shows that as $P_{cent}$ increases, the loss of fluid is from pores with $P_c < P_{cent}$ and the right side of the pore size distribution gradually moves left, and the left side of the pore size distribution remains largely unchanged.

In the literature, the use of the term capillary pressure can be confusing because it can refer to the experimentally applied pressure or the property of the rock sample. In this disclosure, the term $P_{cent}$ refers to experimentally applied pressure, and the term capillary pressure $P_c$ refers to the material properties of a porous medium or pore component thereof.

Furthermore, the capillary pressure $P_c$ of the non-wetting fluid in the centrifuge operations can be related to an effective pore throat radius R by the relations of Eqns. (2) and (3) as set forth above.

By combining Eqn. (2) and Eqn. (8), the capillary pressure $P_c$ can be related to the NMR T2 by the following relation:

$$P_c = \frac{B}{T_2}, \qquad \text{Eqn. (9)}$$

where B is a parameter that combines all the constants such as the interfacial tension γ, the wetting angle θ and possibly a pore shape parameter.

Figure 5B:
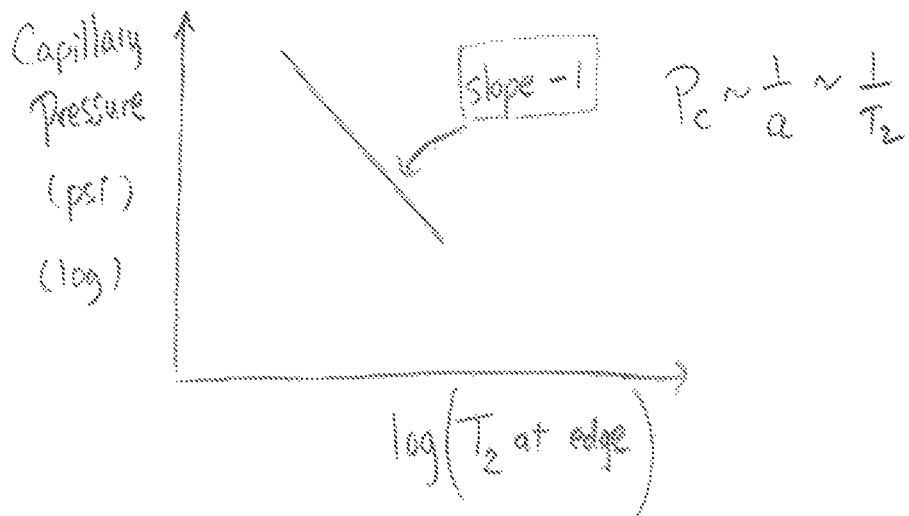
FIG. 5B is a plot of the expected $T_2$ value at the right edge of the $T_2$ frequency distributions (or T2edge) of FIG. 5A as a function of capillary pressure as characterized by applied experimental capillary pressure $P_{cent}$.

The relation of Eqn. (9) can be confirmed by experimental results by plotting the right edge (T2edge) of the $T_2$ frequency distribution functions as a function of capillary pressure characterized by $P_{cent}$ as shown in FIG. 5B. In this plot, the right edge (T2edge) of each $T_2$ frequency distribution corresponds to those pores with pore size characterized by T2edge and a capillary pressure characterized by $P_{cent}$. The plot is expected to follow the behavior of a line with a slope of −1 as indicted in FIG. 5B.

Figure 6A:
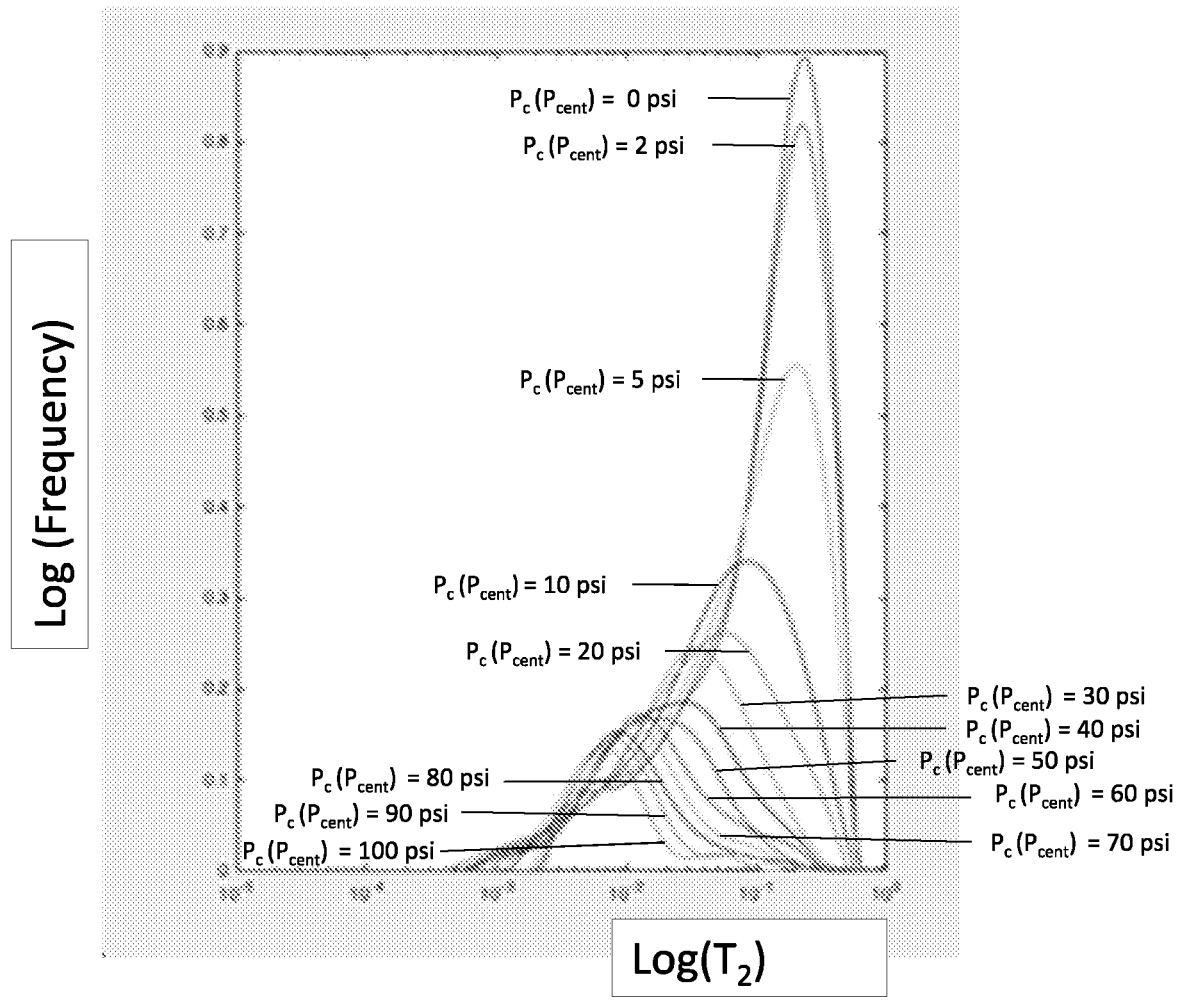
FIG. 6A is a plot of $T_2$ frequency distributions of a Berea sandstone sample measured at progressively higher capillary pressures as characterized by the $P_{cent}$ pressures (from 2 to 100 psi)
Figure 6B:
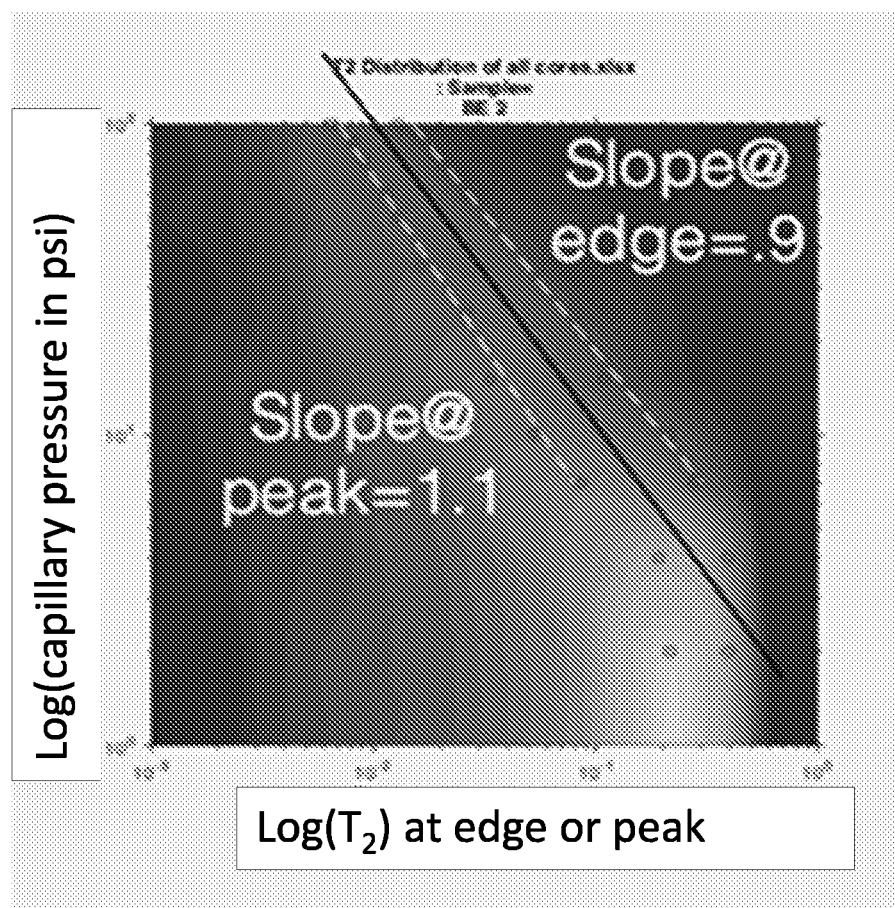
FIG. 6B is a plot of the $T_2$ frequency distributions of the Berea sandstone sample of FIG. 6A as a function of capillary pressures as characterized by the $P_{cent}$, with log($T_2$) as the dimension of the X-axis and log($P_{cent}$) as the dimension of the Y-axis. It also shows $T_2$ values for the peaks and T2edges of the T2 frequency distributions.

This expected behavior is observed in the experimental results of FIGS. 6A and 6B. FIG. 6A are plots of the $T_2$ frequency distributions of a Berea sandstone sample measured at progressively higher capillary pressures as characterized by the $P_{cent}$ pressures (from 2 to 100 psi). FIG. 6B is a grey scale plot of the $T_2$ frequency distributions (with log($T_2$) as the dimension of the X-axis) as a function of capillary pressures as characterized by the $P_{cent}$ (with log ($P_{cent}$) as the dimension of the Y-axis). The $T_2$ value for the peaks and T2edges of the $T_2$ frequency distributions are shown. The slope of the $T_2$ peaks as a function of capillary pressure is −1.1, and the slope of the T2 edges as a function of capillary pressure is −0.9. Thus, the experimental results agree well with the expected behavior. Note that as the applied centrifuge pressure increases, the right edge of the $T_2$ distribution moves to shorter $T_2$ values. This indicates that as the applied centrifuge pressure increases, the pores indicated by the larger $T_2$ values are emptied and thus the signal at longer $T_2$ decreases.

For a particular pore with a capillary pressure of $P_c$, when $P_{cent} < P_c$ the pore remains saturated. When $P_{cent} > P_c$, the pore will be drained. This behavior can be modeled by a step function $S_w$:

$$S_w(P_{cent}, P_c) = \begin{cases} 1, & \text{w en } P_{cent} \leq P_c \\ 0, & \text{w en } P_{cent} > P_c \end{cases}, \qquad \text{Eqn. (10)}$$

where $S_w$ is the saturation of the pore. This function is called Heaviside step function, $S_w = H(P_c \; P_{cent})$ In porous materials, pores of the same volumetric size may have a range of pore throat size and thus a range of $P_c$. This can be accounted for by modifying Eqn. (10) as follows:

$$S_w(P_{cent}, P_c) = \int dP_c' \cdot H(P_c' - P_{cent}) g(P_c, P_c'), \qquad \text{Eqn. (11)}$$

where $P_c'$ represents variance of pore throat size for a given $P_c$, and $g(P_c, P_c')$ is the throat size distribution as a function of $P_c$. For example, one may assume that g is a Gaussian function of the form:

$$g(P_c, P_c') = \exp\left[-\frac{(P_c - P_c')^2}{2\delta^2}\right], \qquad \text{Eqn. (12)}$$

where δ is the width of the capillary pressure distribution in the unit of pressure. Other functional forms of $g(P_c, P_c')$ can be used. For example, FIGS. 7A and 7B illustrate forms of $g(P_c, P_c')$ given as:

$$g(P_c, P_c') = \exp\left[-\frac{(\log(P_c) - \log(P_c'))^2}{2\delta^2}\right]. \qquad \text{Eqn. (13)}$$

Figure 7A:
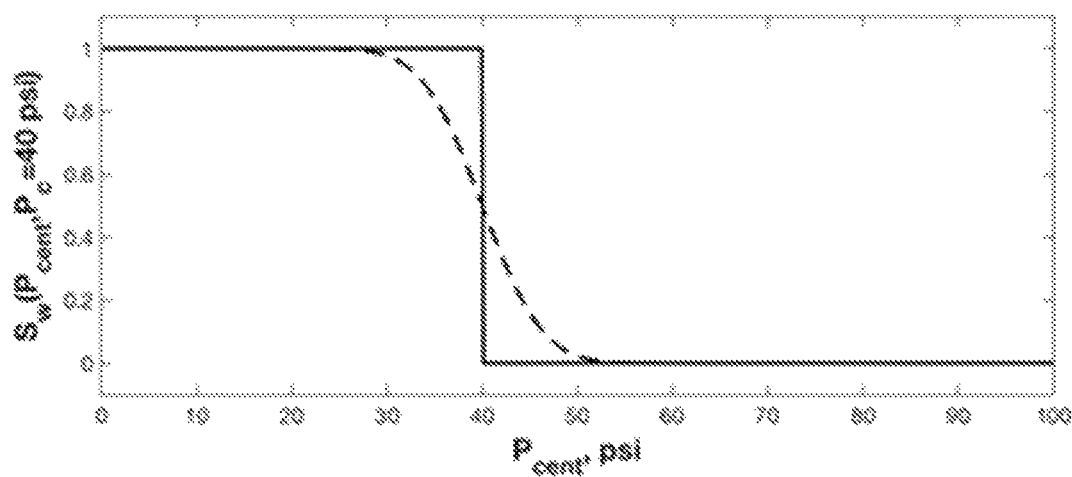
FIG. 7A is a plot (shown in solid line) of an exemplary step-wise function that represents saturation of pore sample as a function of applied experimental capillary pressure $P_{cent}$ as well as a plot (shown in dotted line) of an exemplary modified step-wise function that represents saturation of pore sample as a function of applied experimental capillary pressure $P_{cent}$ with variance of pore throat size for a given $P_c$.
Figure 7B:
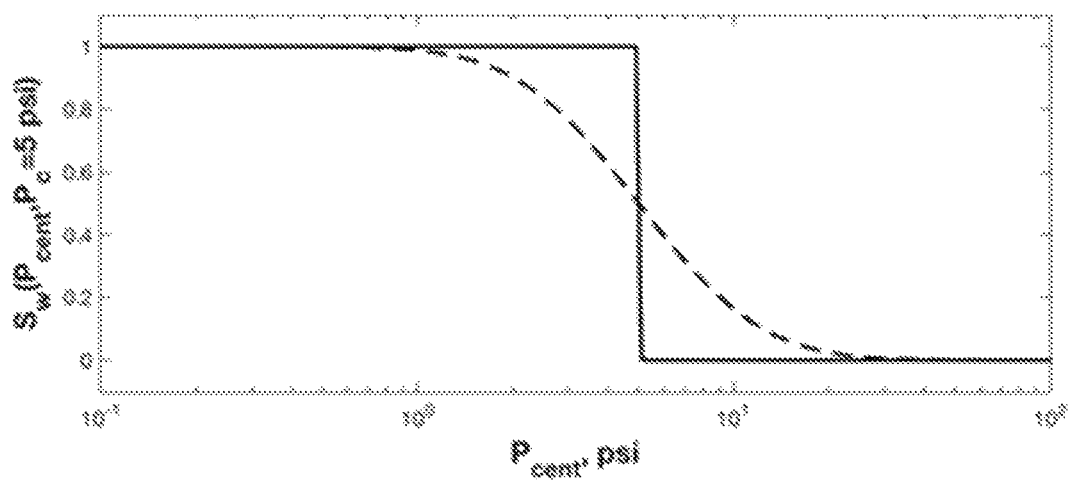
FIG. 7B is a plot (shown in solid line) of an exemplary step-wise function that represents saturation of pore sample as a function of applied experimental capillary pressure $P_{cent}$ as well as a plot (shown in dotted line) of an exemplary modified step-wise function that represents saturation of pore sample as a function of applied experimental capillary pressure $P_{cent}$ with variance of pore throat size for a given $P_c$.

Note that FIG. 7A shows $S_w(P_{cent}, P_c)$ in the linear horizontal axis with $P_c = 40$ psi and δ of 5 psi. The solid line corresponds to Eqn. (10) with a single value of the capillary pressure. The dashed line corresponds to Eqns. (11) and (12). FIG. 7B shows $S_w(P_{cent}, P_c)$ in log scale on the linear horizontal axis with $P_c$ of 40 psi and δ of 5 psi. The solid line corresponds to Eqn. (10) with a single value of the capillary pressure. The dashed line corresponds to Eqns. (11) and (13).

A real porous material would have a range of volumetric pore sizes where each pore size (characterized by $T_2$) is characterized by a pore throat size (which is characterized by its $P_c$). As a result, the NMR signal acquired at a specific $P_{cent}$ can be written as an integral function of the relevant range of $T_2$ values and $P_c$ values as follows:

$$M(t, P_{cent}) = \int\int dT_2 dP_c f(T_2, P_c) S_w(P_{cent}, P_c) \exp\left[-\frac{t_{echo}}{T_2}\right], \qquad \text{Eqn. (14)}$$

where $f(T_2, P_c)$ is the probability distribution of pores with the specific $T_2$ and $P_c$. This distribution function $f(T_2, P_c)$ is the parameter that characterizes the volumetric pore sizes and their flow connectivity. Now we will describe how to acquire experimental data, perform inversion to obtain this distribution function $f(T_2, P_c)$, and use the solved-for distribution function $f(T_2, P_c)$ to characterize properties of a rock sample.

Experimental Workflow

Figure 1:
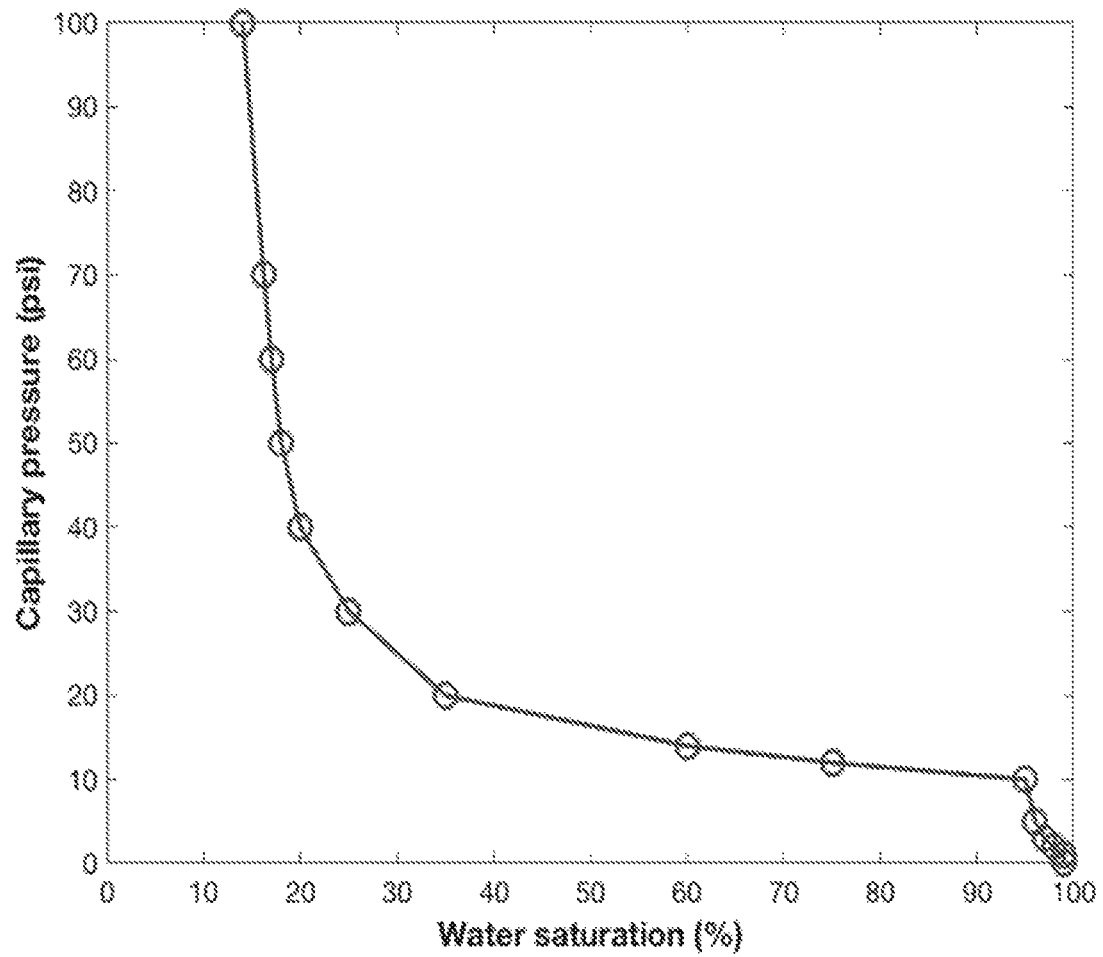
FIG. 1 is an exemplary plot of capillary pressure of a porous rock sample as a function of water saturation measured from a prior art centrifuge experiment.
Figure 14A:
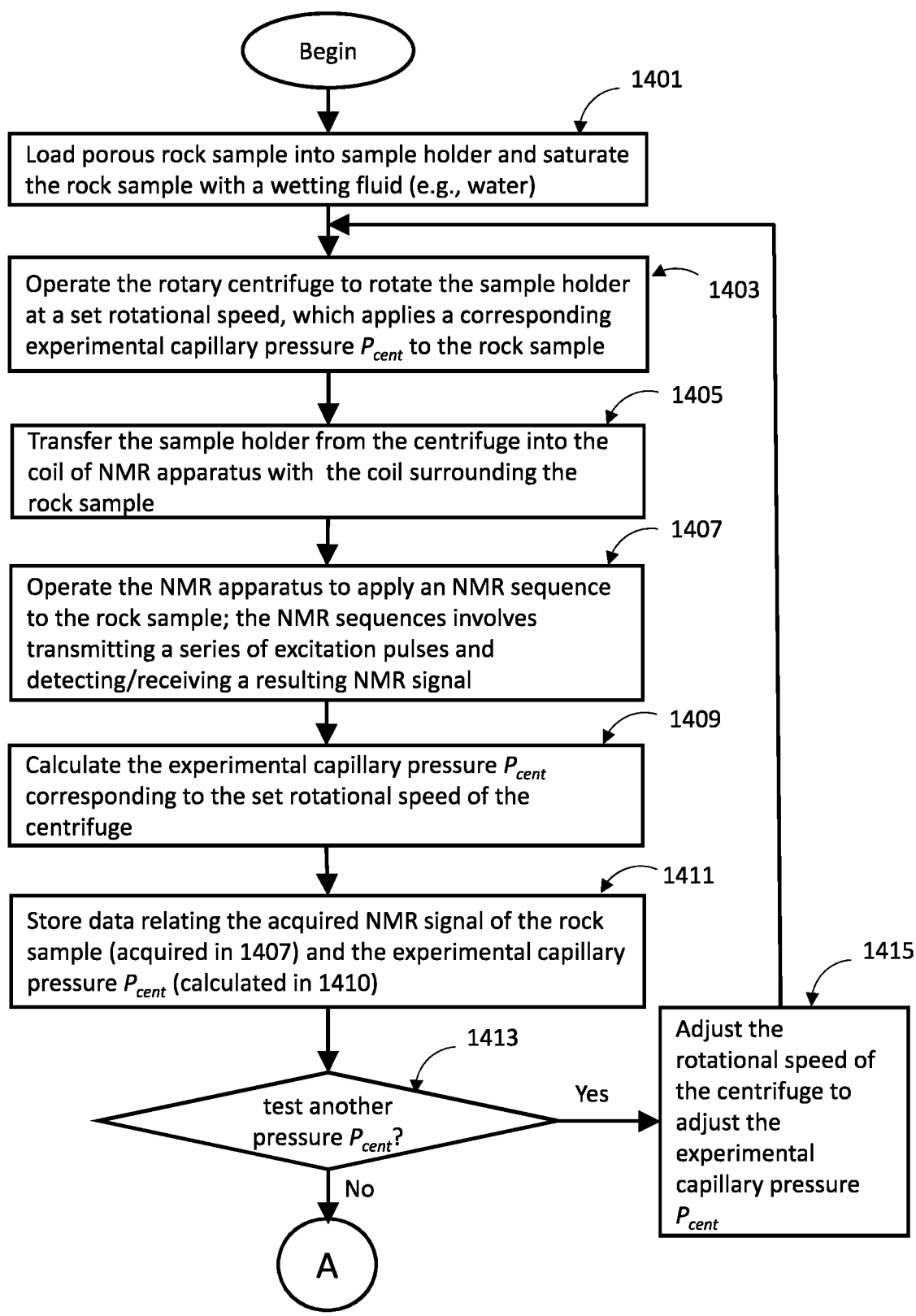
FIGS. 14A and 14B, collectively, is a flow chart that illustrates an experimental workflow in accordance with an embodiment of the present disclosure.
Figure 14B:
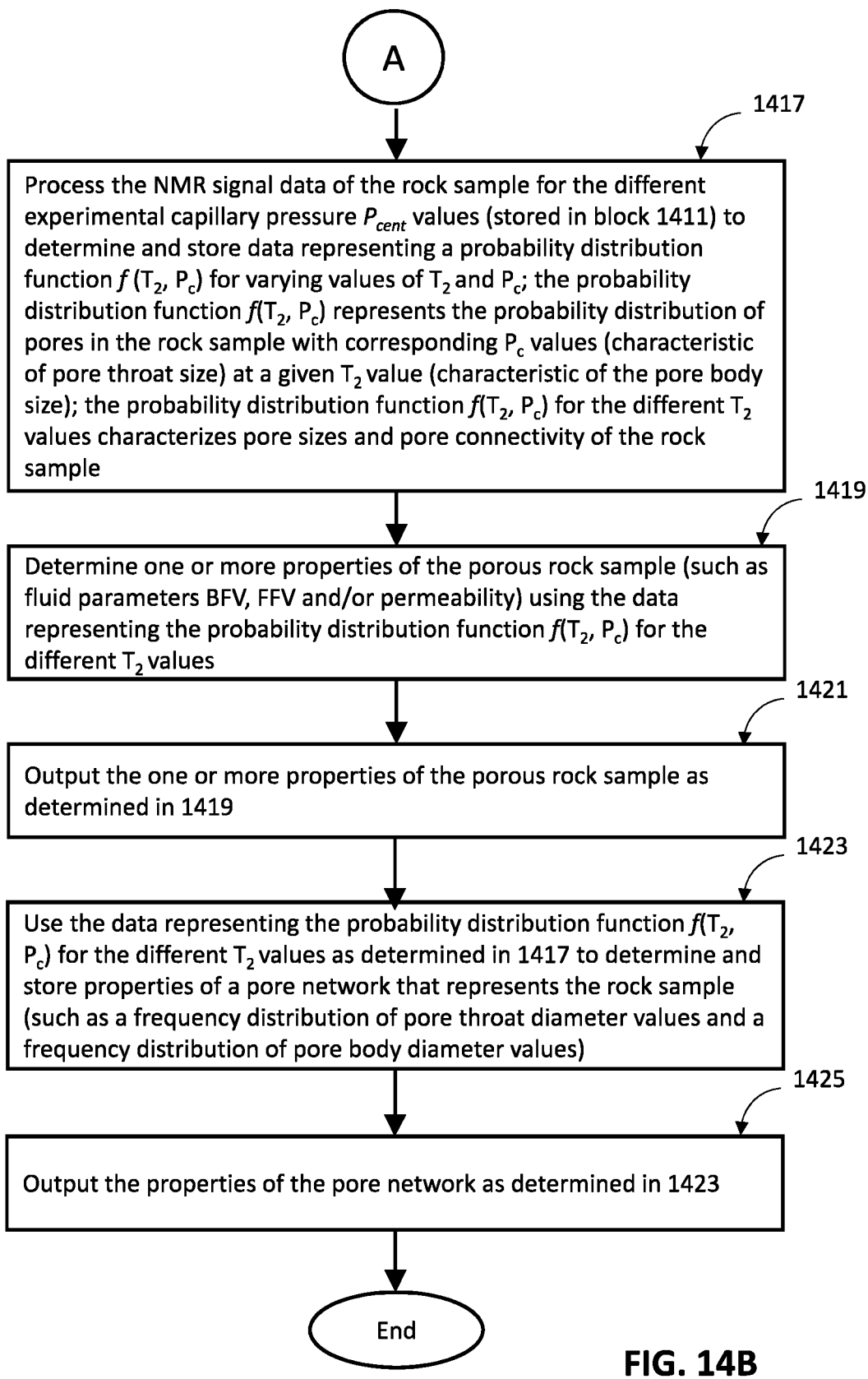

FIGS. 14A and 14B, collectively, is a flow chart that illustrates an experimental workflow in accordance with an embodiment of the present disclosure. The workflow begins in block 1401 where a porous rock sample is loaded into the sample holder 9 of FIG. 1. The porous rock sample is saturated with a wetting fluid (e.g., water) if not done so already. In embodiments, the porous rock sample can be a cylindrical rock core plug, cuttings (e.g., drill cuttings) or other rock sample.

In block 1403, the rotary centrifuge (FIG. 1) is operated to rotate the sample holder 9 at a set rotational speed, which applies a corresponding experimental capillary pressure $P_{cent}$ to the rock sample per Eqn. (4).

In block 1405, after the centrifuge operations are complete, the sample holder is transferred from the centrifuge into the coil 113 of the NMR apparatus (FIG. 3) with the coil 113 surrounding the rock sample.

In block 1407, the NMR apparatus (FIG. 3) is operated to apply an NMR sequence to the rock sample. The NMR sequences involves transmitting a series of excitation pulses and detecting/receiving a resulting NMR signal. In embodiments, the echo time $t_{echo}$ for the NMR measurements can be in the range of 1 ms to 1000 ms with 1000 or more values. Other configurations can also be used for the echo time.

In block 1409, the data processor 125 of FIG. 3 (or some other data processor) calculates the experimental capillary pressure $P_{cent}$ corresponding to the set rotational speed of the centrifuge. Such calculations can be based on Eqn. (4) with the angular velocity ω of the rotation of the rock sample given as input.

In block 1411, the data processor 125 of FIG. 3 (or some other data processor) stores data relating the acquired NMR signal (acquired in 1407) and the experimental capillary pressure $P_{cent}$ (calculated in 1410) in the data storage 127.

In block 1413, the workflow determines if another pressure $P_{cent}$ requires testing. For example, a number of pressure values for $P_{cent}$ (e.g., 10 to 30 values) in the range from 1 psi to 100 psi can be tested in iterations of blocks 1401 to 1415. If so, the operations continue to block 1415 to adjust the rotational speed of the centrifuge, to adjust the experimental capillary pressure $P_{cent}$ for the next iteration. If not, the workflow continues to block 1417.

In block 1417, the data processor 125 of FIG. 3 (or some other data processor) processes the NMR signal data for the different experimental capillary pressure $P_{cent}$ values (as stored in block 1411) to determine and store data representing a probability distribution function $f(T_2, P_c)$ for varying values of $T_2$ and $P_c$. The probability distribution function $f(T_2, P_c)$ represents the probability distribution of pores in the rock sample with corresponding $P_c$ values (characteristic of pore throat size) at a given $T_2$ value (characteristic of the pore body size); the probability distribution function $f(T_2, P_c)$ for the different $T_2$ values characterizes volumetric pore sizes and pore flow connectivity of the rock sample.

In block 1419, the data processor 125 of FIG. 3 (or some other data processor) determines one or more properties of the porous rock sample (such as fluid parameters BFV, FFV and/or permeability) using the data representing the probability distribution function $f(T_2, P_c)$ for the different $T_2$ values as determined in block 1417.

For example, as part of block 1419, data characterizing volume of bound fluid (BFV) in the rock sample can be obtained by integrating the data representing the probability distribution function $f(T_2, P_c)$ for the different $T_2$ values along the $P_c$ and $T_2$ dimensions as follows:

$$BFV = \frac{1}{A}\int_{T2min}^{T2max}dT_2 \int_{P_c=P_{c-cut}}^{P_c=P_{c-max}} f(P_c, T_2)dP_c, \qquad \text{Eqn. (15)}$$

where A is the normalization parameter defined as:

$$A = \int_{T2min}^{T2max}dT_2 \int_{P_{c-min}}^{P_{c-max}} f(P_c,T_2)dP_c. \qquad \text{Eqn. (16)}$$

Here, $P_c$-min and $P_c$-max are the minimum and maximum of $P_c$ range, and $P_c$ cut is the capillary pressure at which the fluid is considered bound. T2min and T2max are the minimum and maximum values of $T_2$ for the distribution function and is typically set by user input.

In another example, data characterizing volume of free fluid (FFV) in the rock sample can be obtained by integrating the data representing the probability distribution function $f(T_2, P_c)$ for the different $T_2$ values along the $P_c$ and $T_2$ dimensions as follows:

$$FFV = \frac{1}{A}\int_{T2min}^{T2max}dT_2 \int_{P_c=P_{c-min}}^{P_c=P_{c-cut}} f(P_c, T_2)dP_c. \qquad \text{Eqn. (17)}$$

In still another example, the calculations of bound fluid volume and free fluid volume can be used to obtain data characterizing permeability of the rock sample by the Timur-Coates formula as follows:

$$k = c\Phi^4\left(\frac{FFV}{BFV}\right)^2, \qquad \text{Eqn. (18)}$$

where BFV is the bound fluid volume fraction as described above, FFV is the free fluid volume fraction as described above, FFV=(1−BFV), Φ is porosity of the rock sample and obtained by other methods, and c is a calibration constant.

In another example, data characterizing permeability of the rock sample can be calculated from the mean value of $T_2$ obtained from the $T_2$ frequency distribution (which is described in Kenyon, "Petrophysical Principles of Applications of NMR Logging," Log Analyst, Vol. 38(2), 1997, pg. 21) as follows:

$$k_{SDR} = c\Phi^4 T_{2lm}^2, \qquad \text{Eqn. (19)}$$

where $T_{2lm}$ is the log-mean of the $T_2$. Since it was developed at the Schlumberger facility SDR, it is often referred to as $k_{SDR}$. Note that $T_{2lm}$ can be calculated from a free fluid $T_2$ distribution $f_{FF}(T_2)$, which can be derived by integrating the data representing the probability distribution function $f(T_2, P_c)$ for the different $T_2$ values as follows:

$$f_{FF}(T_2) = \frac{1}{A}\int_{P_c=P_{c-min}}^{P_c=P_{c-cut}} f(P_c, T_2)dP_c. \qquad \text{Eqn. (20)}$$

$T_{2lm}$ can be calculated as:

$$T_{2lm} = \frac{\int \log(T_2)f_{FF}(T_2)dT_2}{\int f_{FF}(T_2)dT_2}, \qquad \text{Eqn. (21)}$$

where the integrations are performed over the range of T2 from T2min to T2max.

In block 1421, the data processor 125 of FIG. 3 (or some other data processor) outputs the one or more properties of the porous rock sample as determined in 1419.

In block 1423, the data processor 125 of FIG. 3 (or some other data processor) uses the data representing the probability distribution function $f(T_2, P_c)$ for the different $T_2$ values as determined in 1417 to determine and store properties of a pore network that represents the rock sample (such as a frequency distribution of pore throat diameter values and a frequency distribution of pore body diameter values).

In block 1425, the data processor 125 of FIG. 3 (or some other data processor) outputs the one or more properties of the pore network as determined in 1423.

Note that a number of possible inversion methods can be used in block 1417 to obtain the data representing a probability distribution function $f(T_2, P_c)$ based on the acquired NMR signal data (M(t, $P_{cent}$)) for the different experimental capillary pressure $P_{cent}$ values (as stored in block 1411). Three exemplary inversion methods are described below.

Inversion Method 1

In the first inversion method, the acquired NMR signal data for the different experimental capillary pressure $P_{cent}$ values (as stored in block 1411) is written or stored in a matrix form $M(t, P_{cent})$ where the number of rows in the matrix M is the number of echoes (N1) and the number of columns in the matrix M is the number of $P_{cent}$ values (N2).

The probability distribution function $f(T_2, P_c)$ can be represented by a matrix F with a number of rows corresponding to a number of $T_2$ values ($N_{T2}$) and a number of columns corresponding to a number of values of $P_c$ ($N_{Pc}$). Note that $N_{T2}$ typically can be given as 100 corresponding to $T_2$ values equally spaced in the log($T_2$) from 1 ms to 1000 ms. Also note that $N_{Pc}$ typically can be given as 100 corresponding to $P_c$ values equally spaced in log($P_c$) from 1 psi to 100 psi. The i-th value of $T_2$ is labeled $T_{2,i}$, and the j-th value of $P_c$ is labeled $P_{c,j}$.

Two matrices, K1 and K2, can be defined as follows. The element (i,j) of K1 is defined to be:

$$K1_{ij} = \exp\left[-\frac{t_i}{T_{2,j}}\right], \quad \text{Eqn. (22)}$$

where $t_i$ is the i-th value of the echo time $t_{echo}$, i=1 to N1. The size of matrix K1 is N1 by $N_{T2}$. K2 is defined as:

$$K2_{kl} = S_w(P_{cent,k}, P_{c,l}), \quad \text{Eqn. (23)}$$

The size of K2 is N2 by $N_{Pc}$. Using the two matrices K1 and K2, the signal equation can be expressed in the matrix form as follows:

$$M = K1 \cdot F \cdot K2^T, \quad \text{Eqn. (24)}$$

where the dot represents matrix multiplication, and $K2^T$ is the transpose of the matrix K2.

Once the data is written in the matrix format of Eqn. (24), a Fast Laplace Inversion can be used to perform the inversion to solve for the probability distribution function $f(T_2, P_c)$ given by the matrix F. Details of the Fast Laplace Inversion is described in U.S. Pat. No. 6,462,542, herein incorporated by reference in its entirety.

Inversion Method 2

In the second inversion method, the acquired NMR signal data of the rock sample for the different experimental capillary pressure $P_{cent}$ values (as stored in block 1411) is written or stored in a one-dimensional vector m where the i-th element of m corresponds to the data acquired with the i-th pair of $t_{echo}$ at $P_{cent}$, labelled $(t, P_{cent})_i = (t_i, P_{cent,i})$. This method is useful for cases where the NMR signal data does not make a full matrix. For example, the echo train does not contain the same number of echoes or the echo times are different.

The probability distribution function $f(T_2, P_c)$ can be represented by a one-dimensional vector f where the j-th element of f corresponds to the j-th pair of $T_2$ and $P_c$, $(T_2, P_c)_j = (T_{2,j}, P_{c,j})$.

A kernel matrix k can be defined as:

$$k_{ij} = S_w(P_{cent,i}, P_{c,j}) \exp\left[-\frac{t_i}{T_{2,j}}\right]. \quad \text{Eqn. (25)}$$

Then, the signal equation can be expressed in vector form as follows:

$$m = k \cdot f. \quad \text{Eqn. (26)}$$

Once the data is written in the vector format of Eqn. (26), various methods can be used to invert this equation and solve for the probability distribution function $f(T_2, P_c)$ given by the vector f. A brief review of such methods can be found in Song et al., "Two-Dimensional NMR of Diffusion and Relaxation, a chapter in Diffusion NMR of Confined Systems: Fluid Transport in Porous Solids and Heterogeneous Materials," edited by Rustem Valiullin, Royal Society of Chemistry, 2016, page 111-155. One method is the regularization method, for example as described in U.S. Pat. No. 6,462,542. The essence of this method is to obtain a solution f that fits the data, and furthermore satisfies other constraints. The solution can be obtained by minimizing the following function:

$$\|m - kf\|^2 + \alpha \|f\|^2, \quad \text{Eqn. (27)}$$

where $\alpha$ is called regularization parameter, and $\| \ldots \|$ is the Frobenius norm of the matrix. The first term is the difference between the data and fit, the second term is called regularization term. The presence of the regularization term produces slightly broader peaks in $f$ and a more stable solution. Many related methods have been used for such inversion including maximum entropy method.

Another general method can be used to find an ensemble, $\{f_i\}$, of solutions that fit the signal equation (Eqn. (26)) within the noise of the experiment, where each element of the ensemble, $f_i$ is a solution. This approach is described in U.S. Pat. No. 9,052,409, herein incorporated by reference in its entirety. Using the solution ensemble, any property of the spectrum can be obtained as well as the statistical uncertainty.

Inversion Method 3

In the third method, the acquired NMR signal data obtained at each $P_{cent}$ can be inverted individually using conventional 1D inversion methods to obtain the $T_2$ frequency distribution at each $P_{cent}$, $D(T_2, P_{cent})$. It is preferable that the size of the $T_2$ vector is kept the same for all the $T_2$ distributions at the different $P_{cent}$ values. Each $T_2$ value (or an integral around a $T_2$ value) can be plotted as a function of $P_{cent}$ as described below with respect to FIG. 9A.

The signal equation for $D(T_2, P_{cent})$ can be written or stored as function of the probability distribution function $f(T_2, P_c)$ by the following:

$$D(T_2, P_{cent}) = \int dP_c f(T_2, P_c) S_w(P_{cent}, P_c). \quad \text{Eqn. (28)}$$

This equation can be rewritten in a matrix form:

$$D = K_D \cdot F. \quad \text{Eqn. (29)}$$

In Eqn. (29), matrix D is defined as $D_{ij} = D(T_{2,i}, P_{cent,j})$. The kernel matrix $K_D$ is defined as:

$$K_{D,ij} = S_w(P_{cent,i}, P_{c,j}). \quad \text{Eqn. (30)}$$

The probability distribution function $f(T_2, P_c)$ is represented by the matrix F with a number of rows corresponding to a number of T2 values and a number of columns corresponding to a number of values of $P_c$.

Once the data is written in the matrix format of Eqn. (29), a conventional 1D Laplace inversion algorithm can be used to invert the signal equation of Eqn. (29) to solve for the probability distribution function $f(T_2, P_c)$ given by the matrix F. For example, the conventional 1D Laplace inversion algorithms is described in Provencher, "Contin: A general purpose constrained regularization program for inverting noisy linear algebraic and integral equations," Comput. Phys. Commun., Vol. 27, 1982, pgs. 229-242.

Experimental Results of the Inversion Methods

Figure 8A:
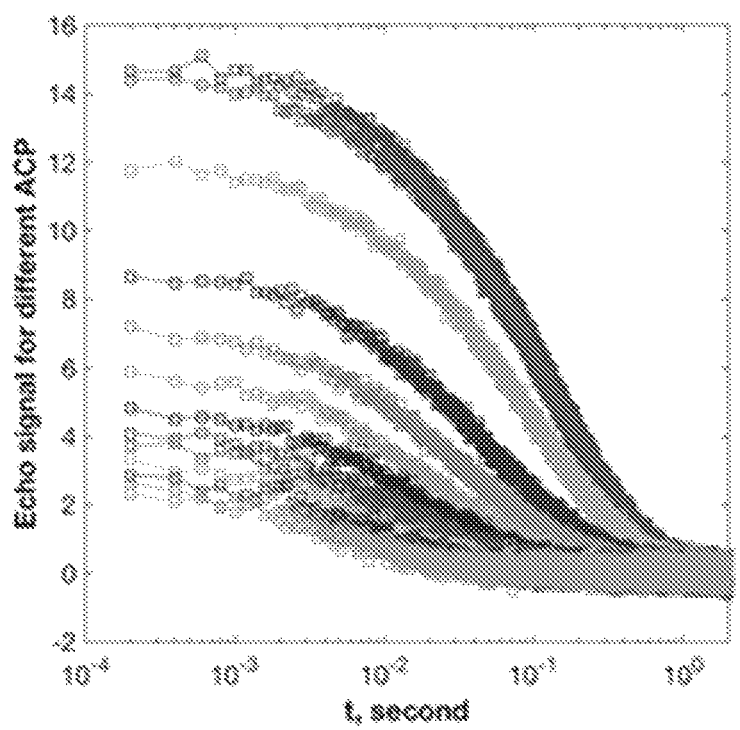
FIG. 8A is a plot of NMR echo signals obtained at a series of $P_{cent}$ values (from 0.1 psi to 100 psi)
Figure 8B:
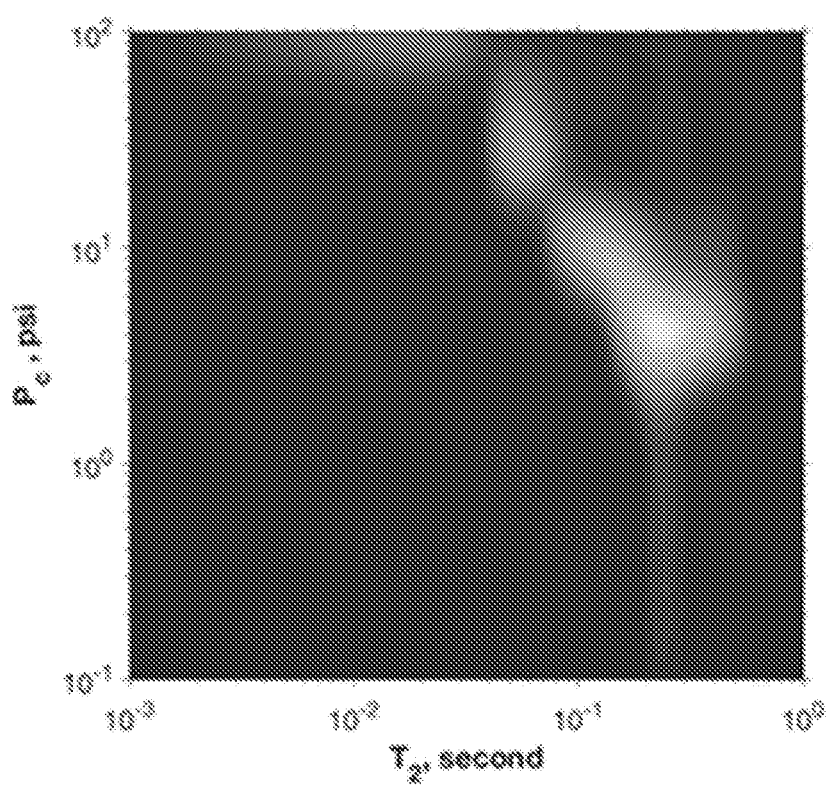
FIG. 8B is a two-dimensional plot (or map) of a probability distribution function $f(T_2, P_c)$ obtained by inversion of the NMR echo signals obtained at a series of $P_{cent}$ values as shown in FIG. 8A.
Figure 8C:
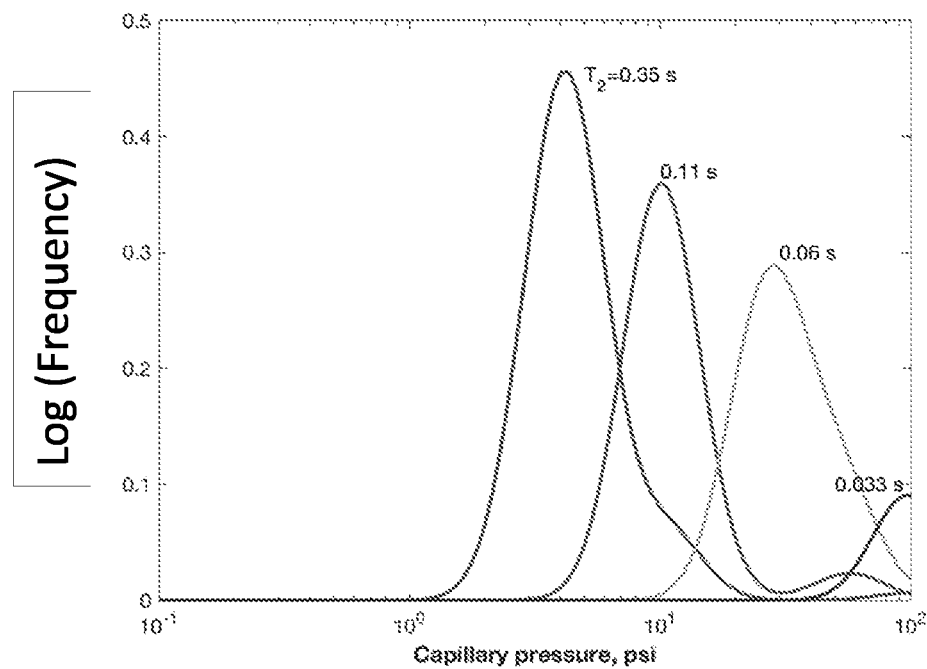
FIG. 8C is a plot of three slices of the two-dimensional map of FIG. 8B for three different $T_2$ values of 0.35 s, 0.11 s, and 0.033 s.

FIGS. 8A, 8B and 8C illustrate experimental results of the inversion method 1 described above. FIG. 8A displays the NMR echo signals obtained at a series of $P_{cent}$ values (from 0.1 psi to 100 psi). A progressive reduction of the echo signal is observed as water is gradually removed/drained from the sample. Also, the decay rate is higher at higher $P_{cent}$ and lower water saturation indicating the water at high $P_{cent}$ is from smaller pores (and thus faster $T_2$).

FIG. 8B shows a two-dimensional plot (or map) of a probability distribution function $f(T_2, P_c)$ obtained from the inversion method 1 described above. It is clear from this plot that the volumetric pore size ($T_2$) and the capillary pressure $P_c$ is highly correlated and pores of longer $T_2$ have lower $P_c$. This behavior can also be seen from the slices of the two-dimensional map of FIG. 8B shown in FIG. 8C, which shows the $P_c$ distribution for several T2 values labeled in the figure. For example, for $T_2=0.35$ s, the $P_c$ is centered at 4 psi, $T_2=0.11$ s at 10 psi, etc. For the very short $T_2$ signals ~ 0.03 s, the $P_c$ is around 100 psi. It is clear that as $T_2$ decreases, the peak of the pore throat size (characterized by $P_c$) also decreases.

Note that FIG. 8C shows frequency distributions of capillary pressure values for several specific T2 values. The frequency distribution of capillary pressure values for a given T2 value can be determined from the slice of the two-dimensional map of FIG. 8B for the given T2 value. Since T2 is directly related to pore size per Eqn. (8) as described above, each one of these curves represents a frequency distribution of capillary pressure values for a corresponding pore size, where the pore size is determined from the T2 value for the curve per Eqn. (8).

Note that these pore-size-specific capillary pressure curves can be converted to a format that is similar to conventional capillary pressure curve, which is derived from an integral form as follows:

$$S_w(P_{cent}, T_2) = \int_{P_{cent}}^{Pcmax} f(P_c, T_2) dP_c,$$  Eqn. (31)

where T2 is a constant.

Figure 9A:
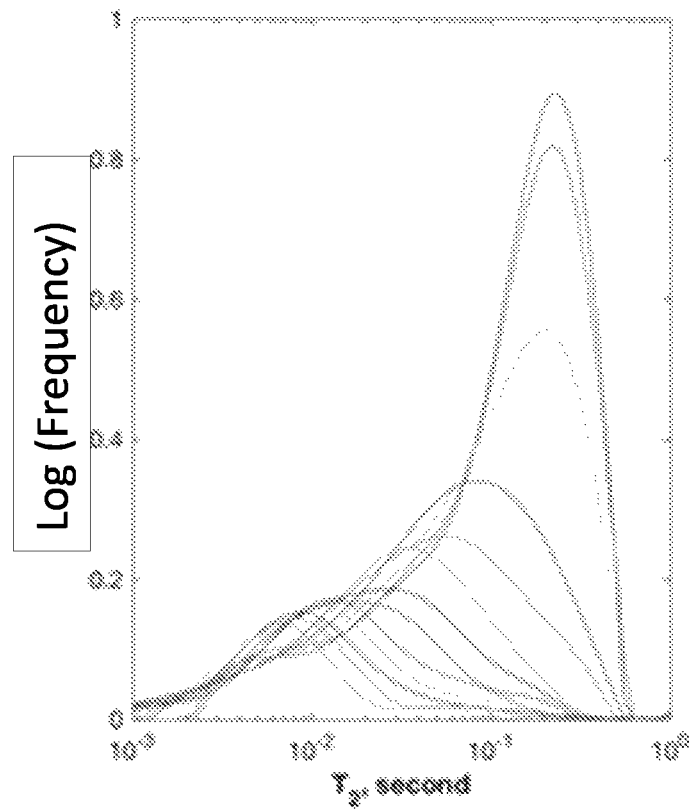
FIG. 9A is a plot of $T_2$ frequency distributions measured at different $P_{cent}$ values.
Figure 9B:
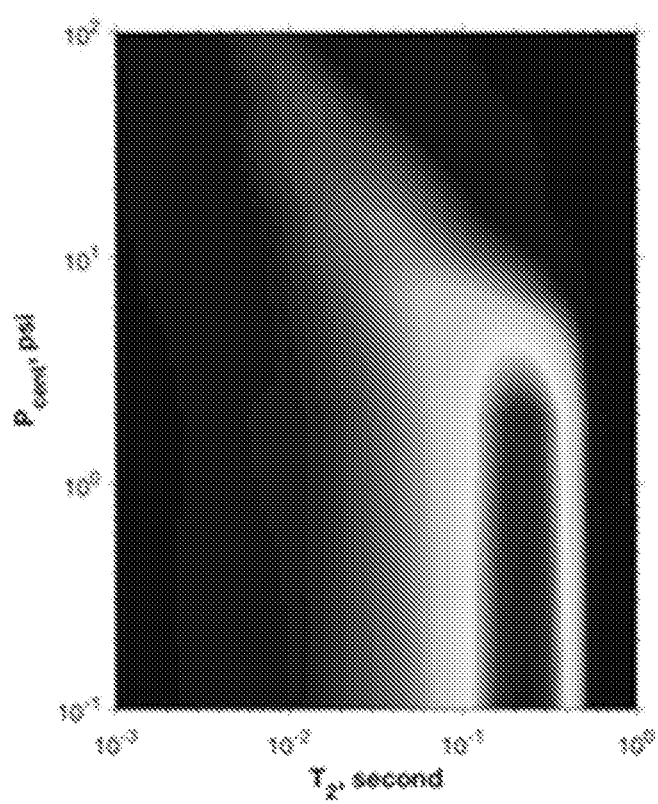
FIG. 9B is a two-dimensional plot (or map) of the $T_2$ frequency distributions of FIG. 9A as a function of $P_{cent}$. The horizontal axis is $T_2$ and the vertical axis is $P_{cent}$.
Figure 9C:
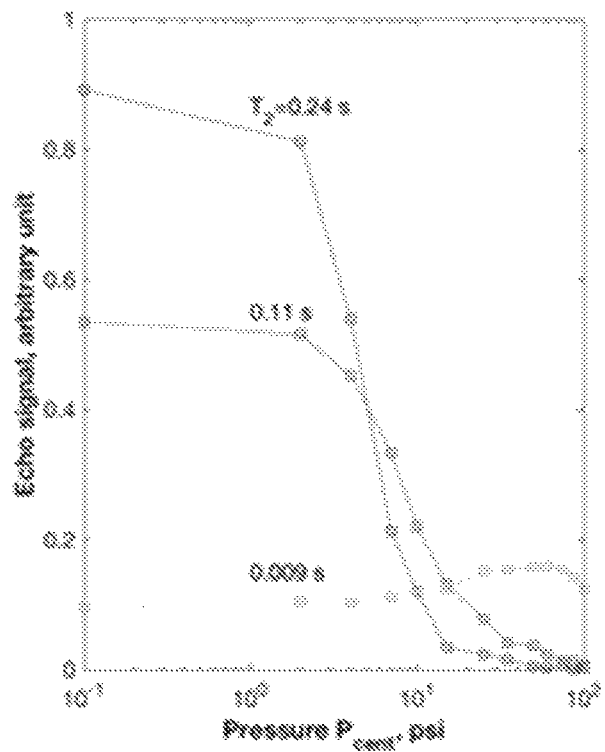
FIG. 9C is a plot of the NMR echo signals at varying $P_{cent}$.

Examples of such conventional capillary pressure curves are shown in FIG. 9C and discussed below.

FIGS. 9A, 9B and 9C illustrate experimental results of the inversion method 3 described above. FIG. 9A is plot of $T_2$ frequency distributions measured at different $P_{cent}$ values. FIG. 9B shows a two-dimensional plot (or map) of the $T_2$ frequency distributions of FIG. 9A as a function of $P_{cent}$. The horizontal axis is $T_2$ and vertical axis is $P_{cent}$. FIG. 9C are plots of the NMR echo signal at varying $P_{cent}$. It shows $P_{cent}$ dependence at several $T_2$ values. It is clear that signal reduction occurs at different $P_{cent}$ for different $T_2$ values. For very short $T_2$ values the signal remains even at the highest pressure (100 psi). This indicates that the pores with short $T_2$ have capillary pressures higher than 100 psi. Furthermore, the plot of FIG. 9C shows that for example, for the $T_2$ value of 0.24 s, most of the drainage occurs at $P_{cent}$ around a few psi. That means the $P_c$ of these pores (characterized by the $T_2$ value) is around a few psi.

Examples of Complex Pore Space

Figure 10A:
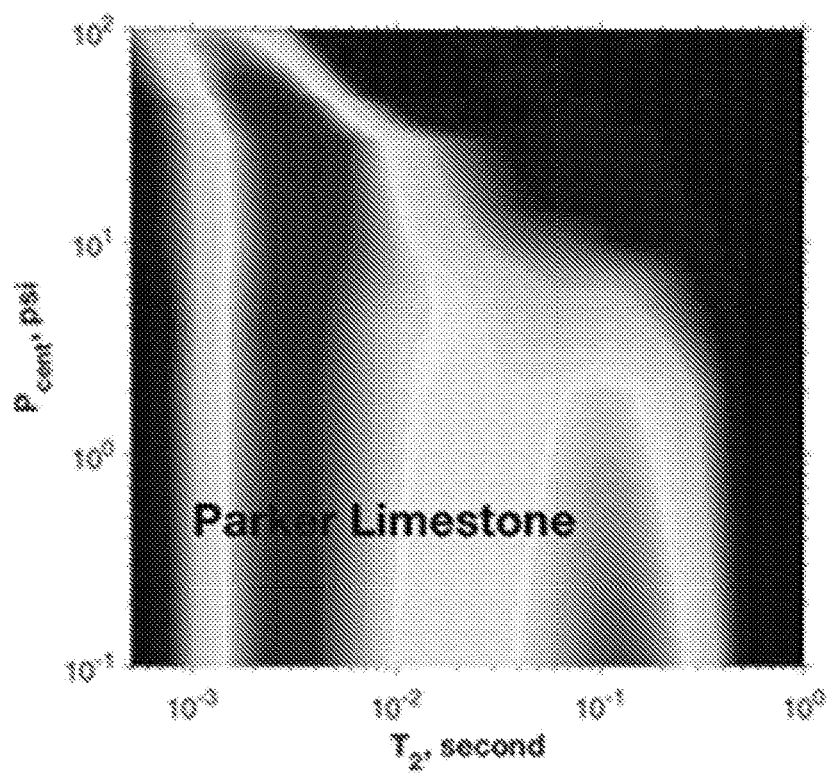
FIG. 10A is a two-dimensional map illustrating a $T_2$ frequency distribution as a function of $P_{cent}$ measured for the Parker limestone.
Figure 10B:
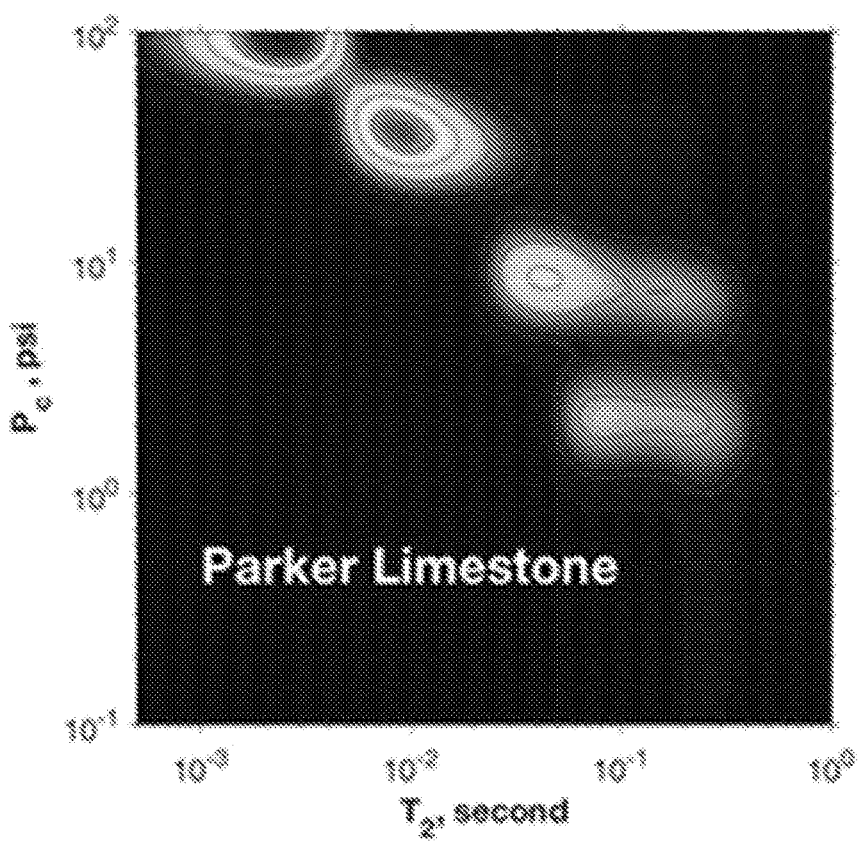
FIG. 10B is a two-dimensional plot (or map) illustrating the probability distribution function $f(T_2, P_c)$ for the Parker limestone corresponding to the $T_2$ frequency distribution of FIG. 10A.
Figure 10C:
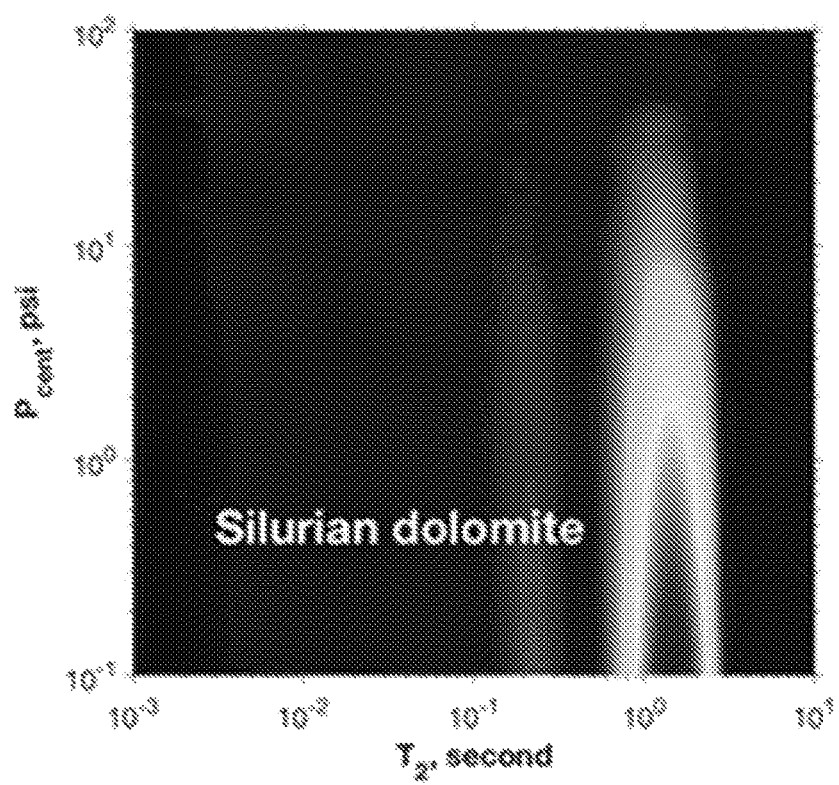
FIG. 10C is a two-dimensional plot (or map) illustrating a $T_2$ frequency distribution as function of $P_{cent}$ measured for the Silurian dolomite.
Figure 10D:
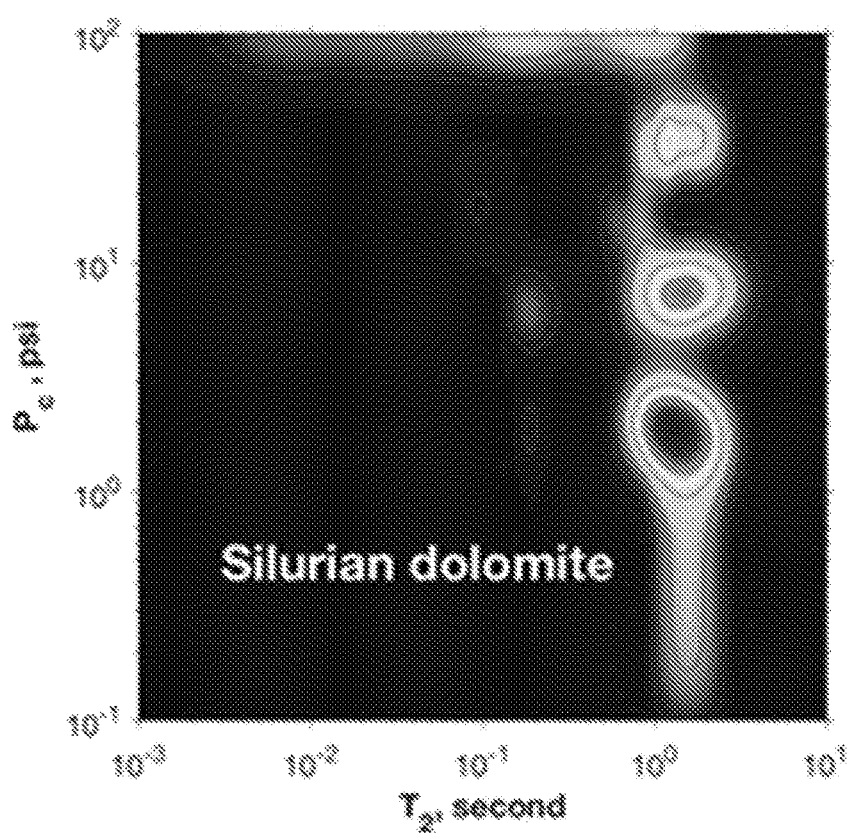
FIG. 10D is a two-dimensional map (or map) illustrating the probability distribution function $f(T_2, P_c)$ for the Silurian dolomite corresponding to the $T_2$ frequency distribution of FIG. 10C.

FIGS. 10A, 10B, 10C and 10D show the experimental results of two rock samples, Parker limestone and Silurian dolomite. FIG. 10A is a two-dimensional map illustrating the $T_2$ frequency distribution as function of $P_{cent}$ measured for the Parker limestone, and FIG. 10B is a two-dimensional map illustrating the corresponding probability distribution function $f(T_2, P_c)$ for the Parker limestone. FIG. 10C is a two-dimensional map illustrating the $T_2$ frequency distribution as function of $P_{cent}$ measured for the Silurian dolomite, and FIG. 10D is a two-dimensional map illustrating the corresponding probability distribution function $f(T_2, P_c)$ for the Silurian dolomite.

The Parker limestone of FIGS. 10A and 10B shows two distinct pore sizes, i.e. larger pores at $T_2$~0.1 s and smaller pores at $T_2$~0.003 s. From the $T_2$ distributions of FIG. 10A, one can see that the larger pores are drained at approximately a few psi pressure. The smaller pores are drained at much higher pressure, 50-100 psi. This behavior is reflected in the two-dimensional map of FIG. 10B, where $P_c$ increases progressively at shorter $T_2$s. This behavior is similar to that of the Berea sandstone example described above with respect to FIGS. 8A, 8B and 8C. A slight difference between the large and smaller pores for Parker limestone is that the $P_c$ distribution is slightly broader at the long $T_2$ component compared to the shorter $T_2$ one.

The Silurian dolomite of FIGS. 10C and 10D shows a behavior that is quite different from both Parker and Berea sandstone. From the $T_2$ distributions of FIG. 10C, one can see that the $T_2$ frequency distribution is dominated by the large peak at $T_2$ around 1-2 s, however, there is a significant fraction of the porosity at shorter $T_2$ over a large range of $T_2$. The large $T_2$ peak progressively decays as $P_{cent}$ increases, but not a sharp drop as in other samples. This indicates that the pore throat size (characterized by $P_c$) for the pores is distributed broadly. This is reflected in the two-dimensional map of FIG. 10D, showing that the $P_c$ distribution is extremely broad for $T_2$~1.5 s, covering the entire 1-100 psi pressure range. The smaller pores with shorter $T_2$ exhibit a Pc~100 psi.

As a result of this complexity in pore connectivity demonstrated by the Silurian rock sample of FIGS. 10C and 10D, it is clear that the bound fluid may not be determined by the $T_2$ frequency distribution of the fully saturated sample. This is because the $T_2$ distribution may underestimate the amount of bound fluid.

Specifically, in sandstone rocks, signals at $T_2$ below 30 ms are considered bound by capillary force and will not produce. Thus, a cutoff value, $T2_{cut}$, e.g., $T2_{cut}=30$ ms is commonly used to calculate the bound fluid volume as follows:

$$BFV = \int_{T2min}^{T2cut} f(T2) dT2,$$  Eqn. (32)

where $f(T2)$ is the $T_2$ frequency distribution, and T2min is the minimum $T_2$ obtained in the $T_2$ distribution. One can assume that $f(T2)$ is normalized as follows:

$$\int_{T2min}^{T2max} f(T2) dT2 = 1.$$  Eqn. (33)

In this case, for the Silurian dolomite rock discussed above, the estimated bound fluid would be 8-10% based on Eqns. (32) and (33) assuming T2cut=30 ms, or 15% assuming T2cut=100 ms. However, the bound fluid measured at $P_{cent}=30$ psi is 38-40%. This is because a fraction of the large $T_2$ signals is bound at $P_{cent}=30$ psi.

It is clear from the above examples that the conventional method to obtain bound fluid and T2cut from T2 frequency distributions alone may be inaccurate dependent on the pore connectivity of individual rocks. For example, for those rocks with a linear correlation of the $P_c$ and $T_2$, such as the Berea sandstone of FIGS. 8A, 8B and 8C and the Parker limestone of FIGS. 10A and 10B, pores of the same size exhibit only one pore throat size and thus $T_2$ is a good indication of the pore throat size (and thus $P_c$). For those rocks, Eqns. (32) and (33) work well and the conventional calibration method would be sufficient.

On the other hand, some rocks (such as the Silurian dolomite of FIGS. 10C and 10D as discussed above) exhibit more complex pore connectivity and one pore size may have a large range of pore throat sizes. In this case, $T_2$ alone may not have sufficient information to determine the bound fluid distribution and the method described herein that combine capillary measurements and inversion of NMR data provide sufficient information to determine the bound fluid distribution.

Construction of Pore Network Model Using the Probability Distribution Function

Figures 11A, 11B, 11C, 11D:
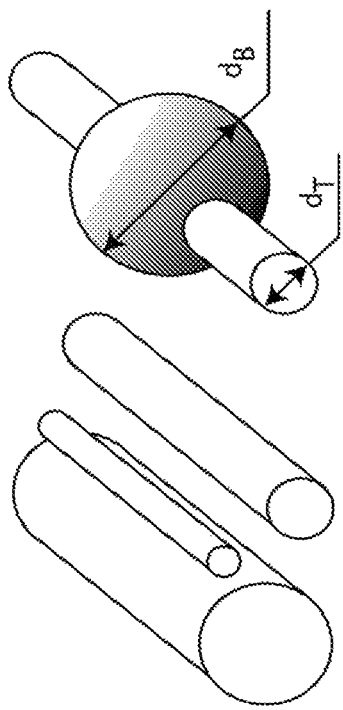
FIG. 11A illustrates an exemplary pore model where the pores of a porous rock are modeled as capillary tubes of different sizes.
FIGS. 11B and 11C illustrate another exemplary pore model where the pores of a porous rock are modeled as spherical pore bodies (of varying diameter $d_B$) with cylindrical pore throats (or varying diameter $d_T$) that connect to other pore bodies.
FIG. 11D illustrates a pore network model including a network of variable-size pore bodies interconnected by variable size pore throats as shown in FIGS. 11B and 11C.

The workflow as described above (e.g., block 1423) can use the data representing the probability distribution function $f(T_2, P_c)$ for the different $T_2$ values to determine and store properties of a pore model that represents the rock sample. The bundle-of-tube model is often used to characterize the pore space in rocks. Such models are often based on the conventional capillary pressure measurements by centrifuge or MICP. In such models, pores are considered to be capillary tubes of different sizes as illustrated in FIG. 11A. The pore model can be extended to include the pore body size and the corresponding pore throat as shown in FIGS. 11B, 11C and 11D. FIG. 11C shows an assemble of pores with a distribution of body sizes with the associated throats. FIG. 11D shows an exemplary pore network model with a number of connected pore bodies and associated pore throats.

The data representing the probability distribution function $f(T_2, P_c)$ for the different $T_2$ values allows one to construct a pore network model with the measured pore body sizes and the associated pore throat sizes and with the measured statistics. This is a significant improvement in pore modelling as compared to the bundle of capillary tubes in understanding the multiphase flow, relative permeability, residue oil saturation, etc.

Hydrocarbon is produced and recovered from formations that consist of heterogeneous rocks exhibiting a wide range of pore geometries. Digital rock technology allows for the acquisition of high-resolution images of a rock sample. Such high-resolution images can be used to quantitatively analyze the complex geological structures of the rock, sedimentary textures and heterogeneous pore systems, and further investigate how they affect fluid flow dynamics. Many tools are available to image rocks with different resolutions. Among them, computerized tomography (CT) and other X-ray scanning technologies are popularly used to create three-dimensional rock images that show the internal pore structures, their connectivity and mineral compositions.

Figure 12A:
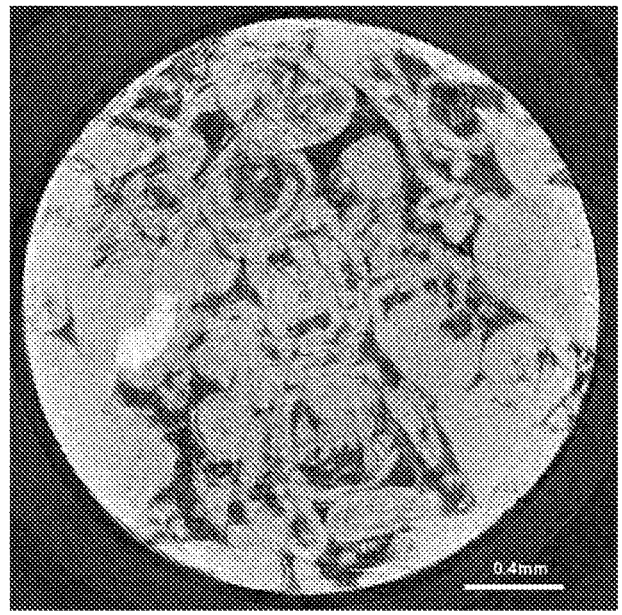
FIG. 12A is a micro-CT image of a limestone sample with a resolution of 2.9 microns.
Figure 12B:
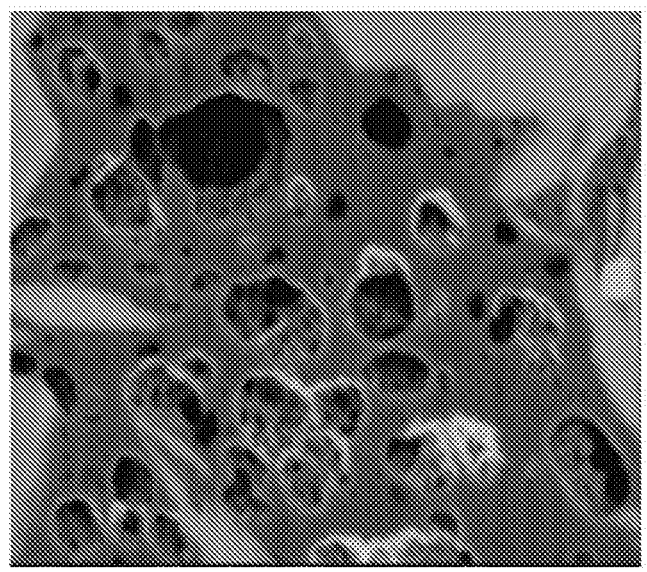
FIG. 12B is an SEM image of a tight shale rock sample.

FIG. 12A shows the micro-CT image of a limestone sample with a resolution of 2.9 microns. The darker area indicates pore space while light and grey areas correspond to solid grains. The diameter of the sample is 2 mm. FIG. 12B is an example of SEM image for a tight shale rock sample, showing both large and small round pores in mature kerogen (darker area) of the shale with a resolution of 3 nm. The size of the sample is 2.0 microns. Even though the pore space in tight shale is very small, it usually serves as main storage for gas in unconventional shale gas reservoirs and leads to gas produced economically once the rock is hydraulically fractured.

Digital rock images are typically gray-scale images, for example, a micro-CT rock image containing continuous variation of intensity attenuation when X-rays pass through a rock sample. More intensity attenuation occurs when a bundle of X-rays penetrates the solid part of the rock such as grains. To identify pore space in a rock sample, a gray-scale image must be segmented into a binary image that includes both pore space and solid matrix of the rock. In practical applications, the threshold that separates pore space from the matrix is determined to ensure the segmented rock porosity matches the laboratory measurement from core plugs.

Figure 13A:
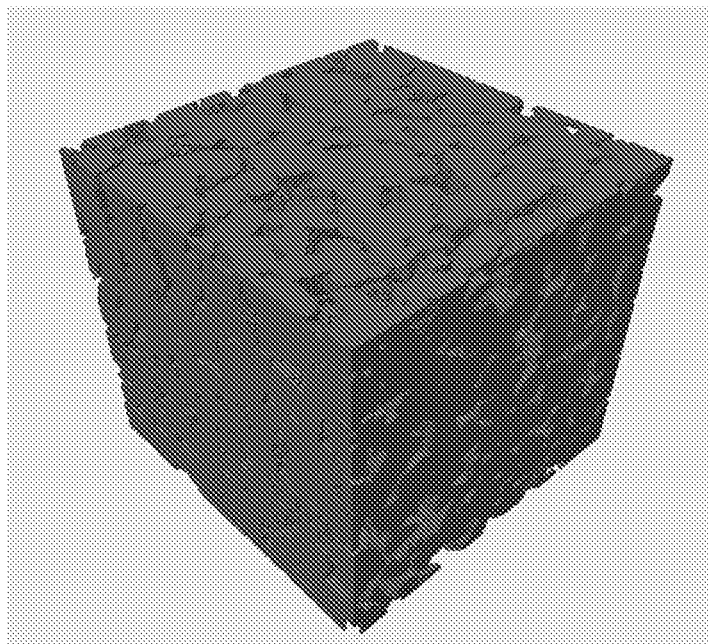
FIG. 13A is a segmented micro-CT image of Fontainebleau sandstone with a resolution of 5.6 microns.

FIG. 13A shows a segmented micro-CT image of Fontainebleau sandstone with a resolution of 5.6 microns. The cubic sample has a size of 1.5 mm with a porosity of 20%. The grains and pore space can be observed in this three-dimensional binary image. Based on the three-dimensional micro-pore structures, single phase or multiphase fluid flow can be simulated on computers to investigate key transport properties associated to the complex rock pore geometries. The studied transport properties could be absolute permeability, relative permeability, capillary pressure, resistivity, formation factor, and other physical responses under a set of specified boundary conditions.

Figure 13B:
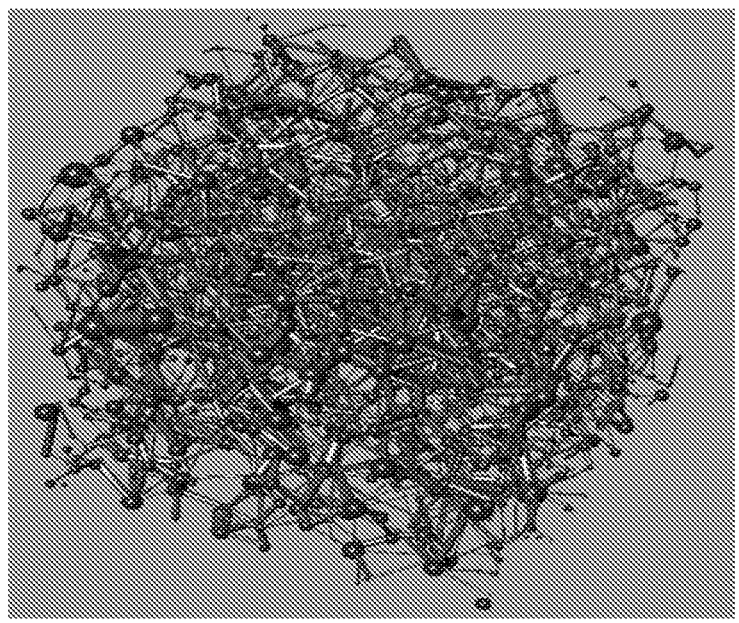
FIG. 13B shows a pore network model extracted from the binary Fontainebleau sandstone sample of FIG. 13A.

There are two ways to compute the transport properties in pore space. One is a direct approach that computes the properties using the Cartesian grid of a binary digital image such as done by Lattice-Boltzmann approach. This direct approach leads to more accurate result but is computationally demanding. An alternative approach is pore network modeling that first extracts a topologically representative network of the pore geometry from the binary digital image and then computes flow and transport properties through the pore network. Details of such pore network modeling is described in Sok et al., "Direct and stochastic generation of network models from tomographic images; effect of topology on residual saturations," Transport in Porous Media, Vol. 46, 2002, pgs. 345-371, and in Blunt et al., "Detailed physics, predictive capabilities and macroscopic consequences for pore-network models of multiphase flow," Advances in Water Resources, Vol. 25, 2002, pgs. 1069-1089. The pore network modeling runs much faster than the direct approach since the computation is done semi-analytically. However, it requires a number of approximations concerning the pore space geometry. FIG. 13B shows a pore network extracted from the binary Fontainebleau sandstone sample in FIG. 13A. In FIG. 13B, the balls represent the pore bodies while tubes connecting the pore bodies represent pore throats.

A challenging topic in digital rock modeling and its application is how to perform upscaling of the properties imaged and modeled from very small samples all the way to reservoir scales given the fact that there may have 12 magnitudes of scale differences in reservoirs and their heterogeneities. Using MPS (multipoint statistics) to combine and model reservoir properties by the aid of digital rock technology is described in Zhang, "MPS-Driven digital rock modeling and upscaling", Math Geosci, Vol. 47, 2015, pgs. 937-954, which discusses both upscaling and downscaling of static and dynamic properties by combing digital rock samples and borehole images using MPS. In modeling the pore network, the pore-throat distribution has significant impact on the resulting transport properties computed based on the geometry such as permeability, oil recovery, wettability study and EOR efficiency screening. A brute force segmentation approach is not sufficient to determine the variability of the diameters of pore space and throat in the imaged rock samples.

In accordance with the present disclosure, distributions of the diameters of pore body and pore throat size of a pore network model can be constrained to follow those measured by NMR and given by the data representing the probability distribution function $f(T_2, P_c)$ for different $T_2$ values as described above. In such analysis, the frame of the primary pore network remains the same (i.e., the positions of the spherical pore bodies and cylindrical pore throats), and the connectivity between pore bodies and pore throats remain the same. However, the diameters of the pore bodies and the diameters of pore throats of the pore network model can be processed and transformed such that they agree with the distributions measured by NMR and given by the data representing the probability distribution function $f(T_2, P_c)$ for the different $T_2$ values as described above.

Figure 15A:
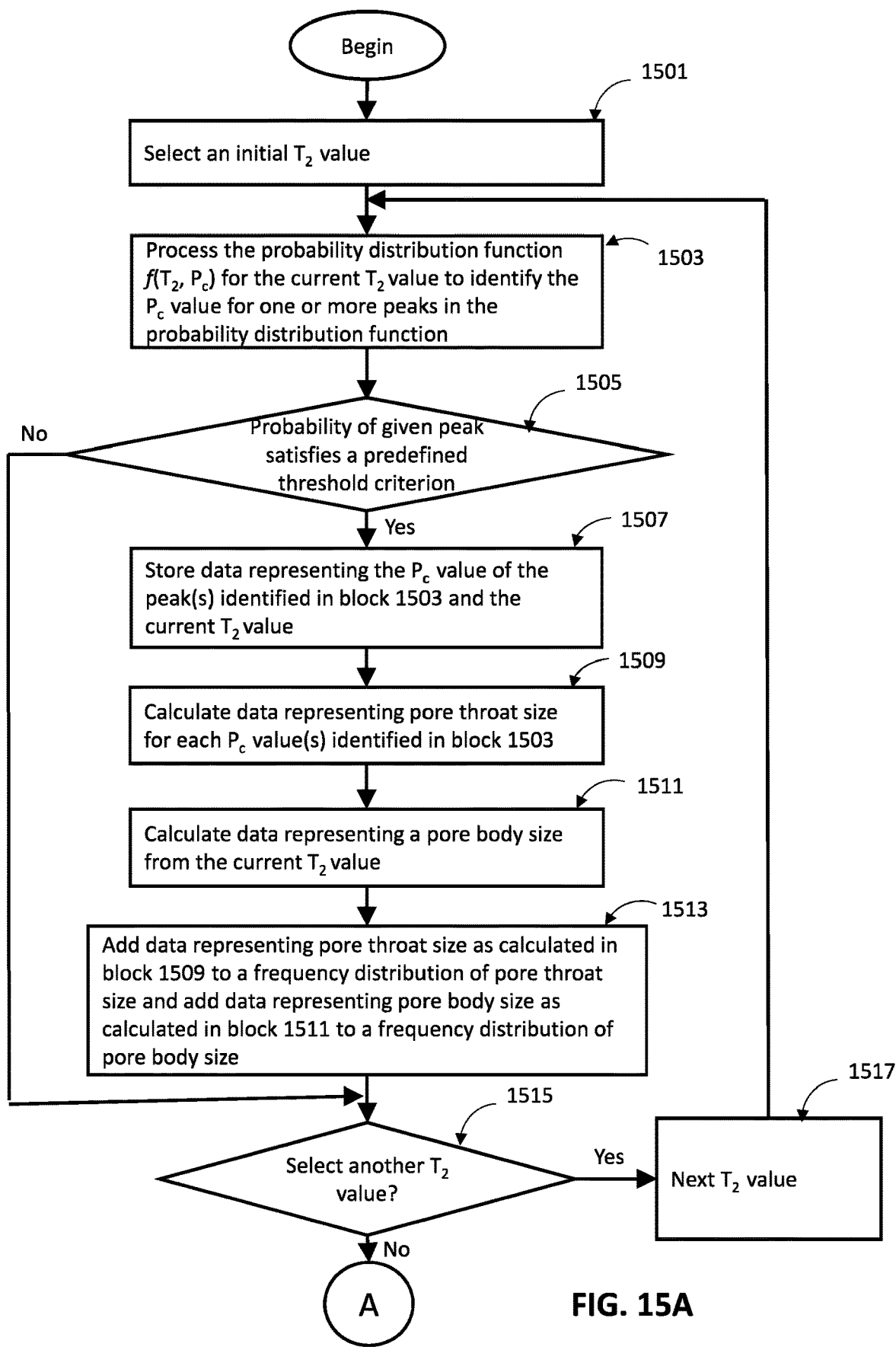
FIGS. 15A and 15B, collectively, is a flow chart that illustrates a workflow that employs a probability distribution function $f(T_2, P_c)$ as a constraint to assign pore body sizes and pore throat sizes of a pore network model in accordance with an embodiment of the present disclosure.
Figure 15B:
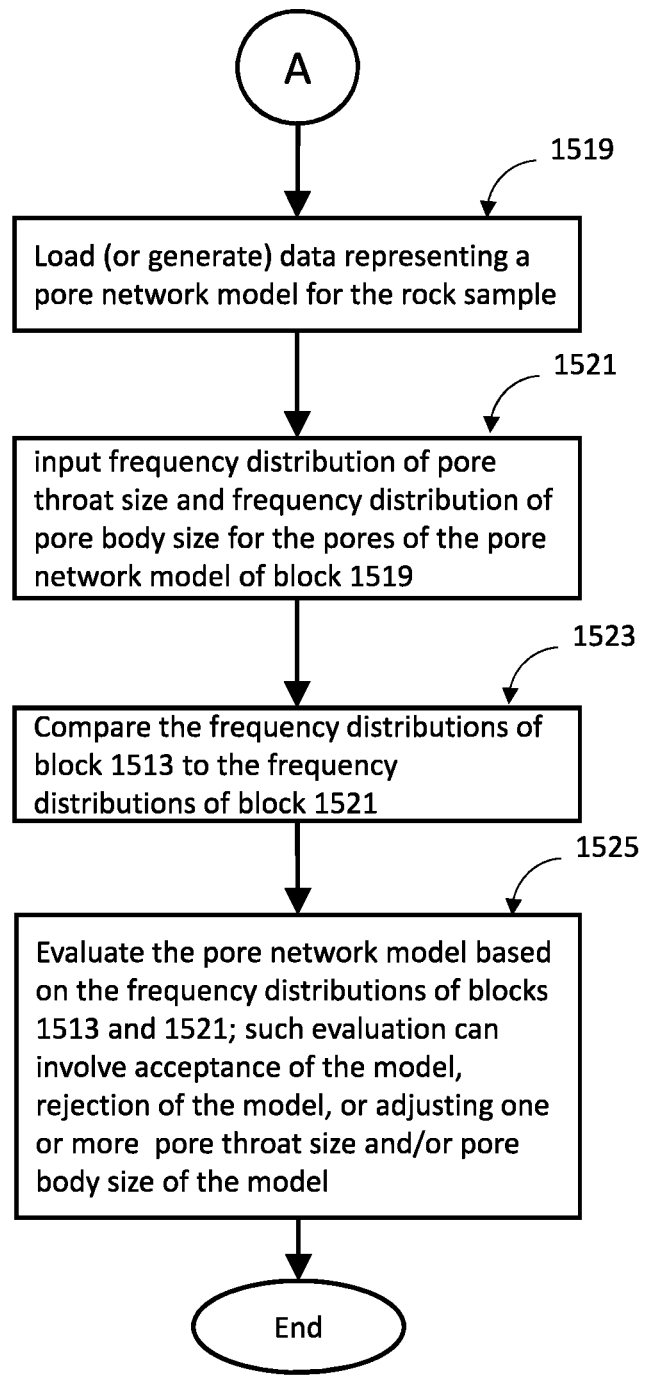

An example workflow that constrains the distributions of the diameters of pore body and pore throat size of a pore network model to follow those measured by NMR and given by the data representing the probability distribution function $f(T_2, P_c)$ for different $T_2$ values is shown in FIGS. 15A and 15B. The workflow can be performed by the data processor 125 of FIG. 3 (or some other data processor).

In block 1501, an initial $T_2$ value is selected from the range of $T_2$ values of the probability distribution function $f(T_2, P_c)$.

In block 1503, the data representing the probability distribution function $f(T_2, P_c)$ for the current $T_2$ value is processed to identify the $P_c$ value for one or more peaks in the probability distribution function $f(T_2, P_c)$ for the current $T_2$ value.

In block 1505, the operations check whether the probability of a given peak satisfies a predefined threshold criterion. For example, the criterion could be that the probability is higher than a predefined value, e.g. 1% of the maximum in the $f(T_2, P_c)$ map. It could also be zero. If so, the operations continue to block 1507. If not, the operations continue to block 1515.

In block 1507, data representing the $P_c$ value of the peak(s) identified in block 1503 and the current $T_2$ value is stored in data storage.

In block 1509, data representing a pore throat size is calculated for each $P_c$ value(s) identified in block 1503. Such calculation can be based on Eqn. (2) or Eqn. (3) as described above.

In block 1511, data representing a pore body size is calculated for the current $T_2$ value. Such calculation can be based on Eqn. (8) where the pore body size is represented by a diameter d and is related to the current $T_2$ value by the relation $1/T_2=4\rho/d$.

In block 1513, the data representing pore throat size as calculated in block 1509 is added to data representing a frequency distribution of pore throat size stored in data storage, and the data representing pore body size as calculated in block 1511 is added to data representing a frequency distribution of pore body size stored in data storage.

In block 1515, the operations check whether there is another $T_2$ value in the range of $T_2$ values in the probability distribution function $f(T_2, P_c)$. If not, the operations continue to block 1519. If so, the operations continue to block 1517 to select the next $T_2$ value in the range of $T_2$ values in the probability distribution function $f(T_2, P_c)$ and the processing continues for another iteration of blocks 1503 to 1515 where the next $T_2$ value is set as the current $T_2$ value.

In block 1519, a pore network model for the rock sample is loaded from data storage (or possibly generated if need be). The pore network model can be derived from segmented images of the rock sample or other similar rock. Exemplary techniques for deriving the pore network model is described in Sok et al., "Direct and stochastic generation of network models from tomographic images; effect of topology on residual saturations," Transport in Porous Media, Vol. 46, 2002, pgs. 345-371, and in Blunt et al., "Detailed physics, predictive capabilities and macroscopic consequences for pore-network models of multiphase flow," Advances in Water Resources, Vol. 25, 2002, pgs. 1069-1089.

In block 1521, data representing a frequency distribution of pore throat size and data representing a frequency distribution of pore body size for the pores of the pore network model of block 1519 is input for processing.

In block 1523, the frequency distributions of block 1513 can be compared to the frequency distributions of block 1521.

In block 1525, the pore network model is evaluated based on the frequency distributions of blocks 1513 and 1521. Such evaluation can involve acceptance of the model, rejection of the model, or adjusting the pore throat size and/or pore body size for pores of the pore network model based on the frequency distributions of blocks 1513 and 1521.

Figure 16:
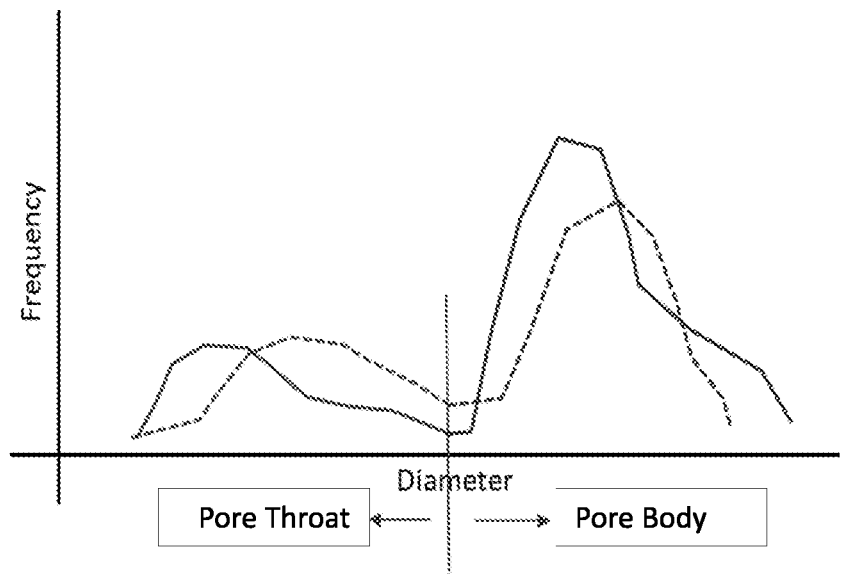
FIG. 16 is a plot of pore throat size distribution and pore body size distribution (dashed lines) for an initial pore network model as well as a plot of pore throat size distribution and pore body size distribution (continuous lines) as determined from a probability distribution function $f(T_2, P_c)$ as part of the workflow of FIGS. 15A and 15B.

FIG. 16 shows plots of exemplary frequency distributions of both pore body sizes and pore throat sizes for an initial pore network model of a rock sample as well as exemplary frequency distributions of both pore body sizes and pore throat sizes that are generated from the probability distribution function $f(T_2, P_c)$ as described herein and used to adjust or otherwise constrain the pore body sizes and pore throat sizes for the pore network model.

Figure 17:
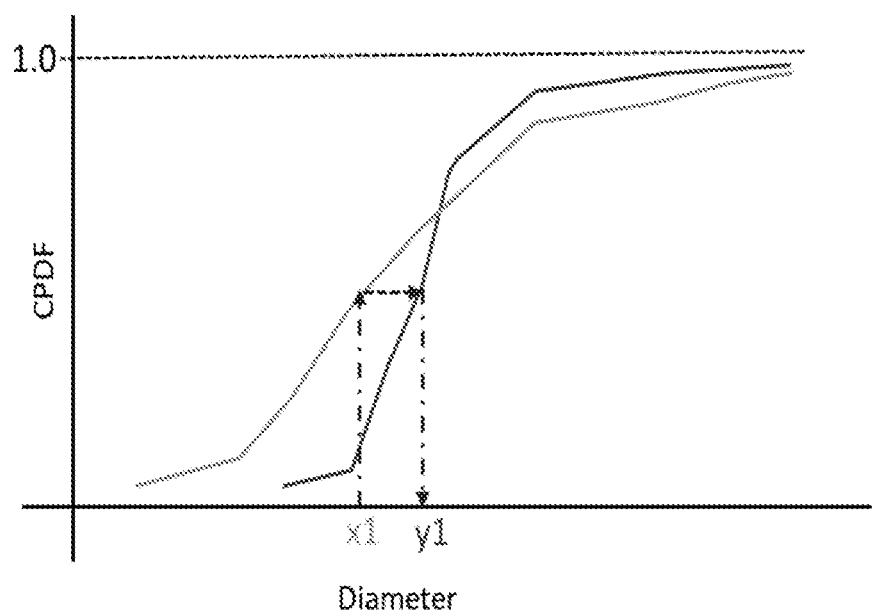
FIG. 17 is a schematic illustration of an exemplary method that replaces a pore throat size or pore body size of the initial pore network model with a pore throat size or pore body size determined from a probability distribution function $f(T_2, P_c)$ on a per-sample basis.

FIG. 17 is a diagram that illustrates a method that uses the pore body sizes and pore throat sizes that are generated from the probability distribution function $f(T_2, P_c)$ to adjust or constrain the pore body sizes and pore throat sizes for a pore network model of a rock sample. The method follows a Monte Carlo approach. In order to adjust the pore body sizes of the pore network model, a pore body size value or sample "x1" is randomly drawn from the initial pore body size frequency distribution of block 1521, the CPDF (cumulative probability density function) value of the sample x1 is identified by tracing vertically to the CPDF, the CPDF value of the corresponding measured pore body size frequency distribution of block 1513 is identified by tracing horizontally), a pore body size value or sample "y1" in the measured pore body size frequency distribution of block 1513 is identified by moving downward from such CPDF value, and the pore body size value "y1" replaces the value "x1" for the pore body size of the initial pore network. Similar operations that involve samples from the initial pore throat size frequency distribution of block 1521 and the measured pore throat size frequency distribution of block 1513 can be performed to adjust the pore throat sizes of the pore network model. The number of samples that is processed for each case can be selected as desired. This distribution transformation is rank-preserving, i.e. it keeps the ranking order of the samples during the transformation while enforcing the matching of a target distribution. This approach can be used for transforming both the distributions of the sizes (or diameters) of pore bodies and pore throats of the pore network model.

In the embodiments described above, the acquired NMR signal data is processed to determine NMR property values related to transverse relaxation time (T2) of hydrogen protons, which is often obtained by a CPMG pulse sequence. Other pulse sequences can also be used to obtain values for other NMR properties of the rock sample, such as inversion recovery sequence to obtain longitudinal relaxation time (T1) values, pulsed field gradient experiment to obtain diffusion coefficient (D) values. Several other multi-dimensional experiments have also been used extensively in petroleum sciences to characterize two dimensional maps of NMR property values of the rock sample, such as inversion-recovery-CPMG experiment for a T1-T2 map, and a diffusion editing-CPMG experiment for a D-T2 map. These methods can all be performed at different capillary pressures to obtain a range of NMR properties of the rock sample as a function of capillary pressure values. Furthermore, such NMR properties can be processed by inversion methods to determine a probability distribution function of capillary pressure values as a function of NMR property values, and the probability distribution function of capillary pressure values as a function of NMR properties values can be processed to determine at least one parameter indicative of one or more properties of the porous rock sample.

Figure 18:
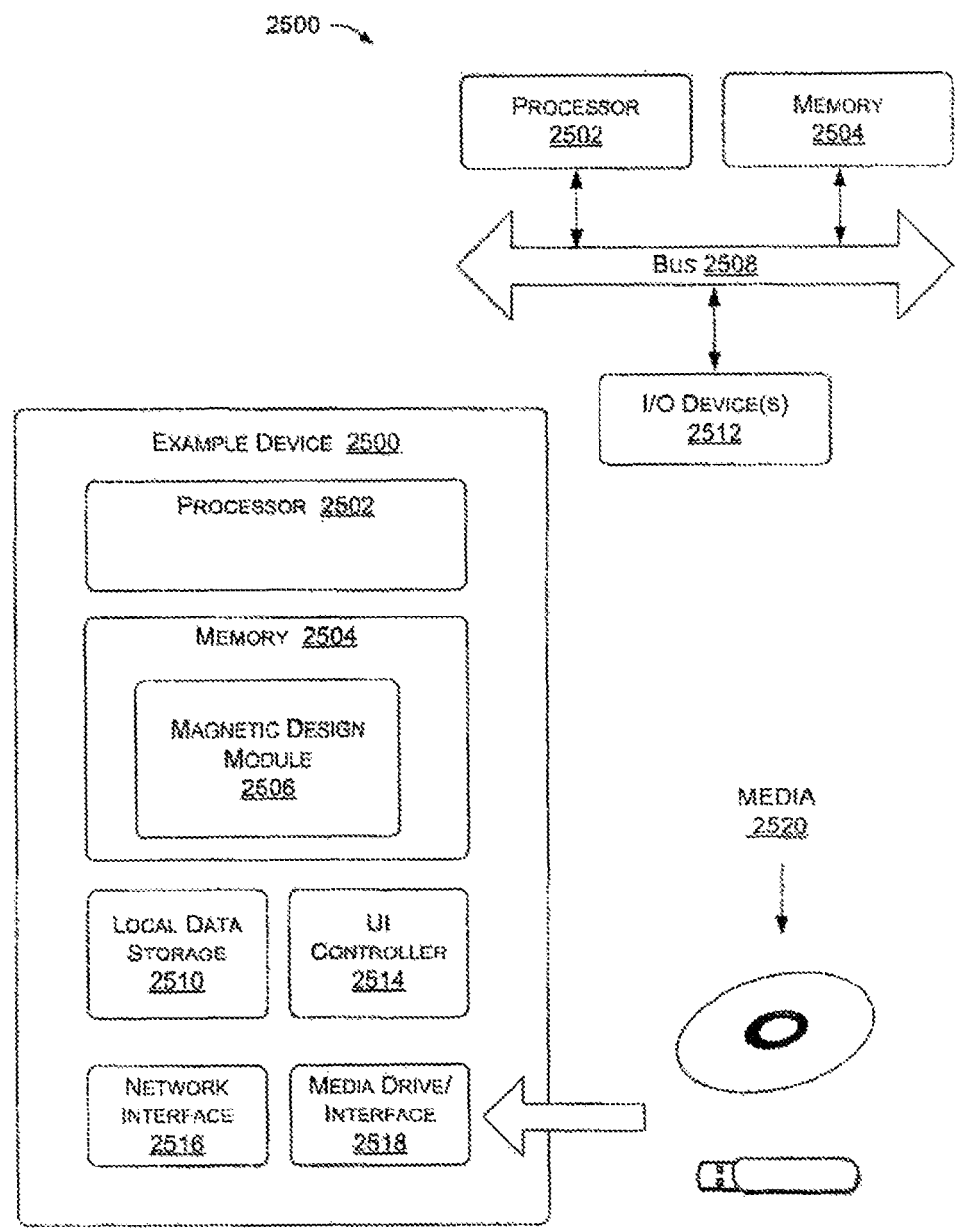
FIG. 18 is a functional block diagram of an exemplary computer processing system.

FIG. 18 illustrates an example device 2500, with a processor 2502 and memory 2504 that can be configured to implement various embodiments of methods as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of a computer, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

Although a few example embodiments have been described in detail above, those skilled in the art will readily appreciate that many modifications are possible in the example embodiments without materially departing from this disclosure. Accordingly, such modifications are intended to be included within the scope of this disclosure. For example, a continuous-flow apparatus can be used as a substitute for the rotary centrifuge to subject the porous rock sample to a desired applied experimental pressure as described herein. Moreover, embodiments may be performed in the absence of any component not explicitly described herein. It will therefore be appreciated by those skilled in the art that yet other modifications could be made to the provided invention without deviating from its spirit and scope as claimed.

What is claimed is:

1. A method of characterizing a porous rock sample, comprising:
    i) subjecting the porous rock sample to an applied experimental pressure where a first fluid that saturates the porous rock sample is displaced by a second fluid; and
    ii) subsequent to the operations of i), applying an NMR pulse sequence to the porous rock sample, detecting resulting NMR signals from the porous rock sample, and generating and storing NMR data representative of the detected resulting NMR signals;
    iii) repeating the operations of i) and ii) over varying applied experimental pressure to obtain NMR data associated with varying applied experimental pressure values;
    iv) processing the NMR data associated with varying applied experimental pressures of iii) to obtain a probability distribution function of capillary pressure values as a function of NMR property values; and
    v) processing the probability distribution function of capillary pressure values as a function of NMR properties values of iv) to determine at least one parameter indicative of the porous rock sample.

2. A method according to claim 1, wherein:
    the NMR property values are selected from the group consisting of: transverse relaxation time (T2) values, longitudinal relaxation time (T1) values, diffusion coefficient (D) values, a two-dimensional map of T1-T2 values, a two-dimensional map of D-T2 values, and a two-dimensional map of D-T1 values.

3. A method according to claim 1, wherein:
the at least one parameter indicative of the porous rock sample comprises a frequency distribution of capillary pressure values for a specific pore size.

4. A method according to claim 1, wherein:
the at least one parameter indicative of the porous rock sample comprises a parameter indicative of bound fluid volume in the porous rock sample.

5. A method according to claim 4, wherein:
the parameter indicative of bound fluid volume in the porous rock sample is derived by integration or addition along dimensions of both transverse relaxation values and the capillary pressure values.

6. A method according to claim 4, wherein:
the parameter indicative of bound fluid volume in the porous rock sample is given as BFV and is calculated as $$BFV = 1/A \int_{T2min}^{T2max} dT_2 \int_{Pc=Pc\text{-}cut}^{Pc=Pc\text{-}max} f(P_c, T_2) dP_c,$$

where A is the normalization parameter defined as $$A = \int_{T2min}^{T2max} dT_2 \int_{Pc\text{-}min}^{Pc\text{-}max} f(P_c, T_2) dP_c,$$

where $f(P_c, T_2)$ is the probability distribution function of capillary pressure values as a function of transverse relaxation values,
Pc represents a dimension of the capillary pressure values,
Pc-max represents a maximum capillary pressure value,
Pc-min represents a minimum capillary pressure value,
Pc-cut represents a capillary pressure value at which fluid is considered bound,
$T_2$ represents a dimension of the transverse relaxation values,
T2max represents a maximum $T_2$ value, and
T2 min represents a minimum $T_2$ value.

7. A method according to claim 1, wherein:
the at least one parameter indicative of the porous rock sample comprises a parameter indicative of free fluid volume in the porous rock sample.

8. A method according to claim 7, wherein:
the parameter indicative of free fluid volume in the porous rock sample is derived by integration or addition along dimensions of both transverse relaxation values and the capillary pressure values.

9. A method according to claim 7, wherein:
the parameter indicative of free fluid volume in the porous rock sample is given as FFV and is calculated as $$FFV = 1/A \int_{T2min}^{T2max} dT_2 \int_{Pc=Pc\ min}^{Pc=Pc\ max} f(P_c, T_2) DP_c,$$

where A is the normalization parameter defined as $$A = \int_{T2min}^{T2max} dT_2 \int_{Pc\ min}^{Pc\ max} f(P_c, T_2) dP_c,$$

where $f(P_c, T_2)$ is the probability distribution of capillary pressure values as a function of transverse relaxation values,
Pc represents a dimension of the capillary pressure values,
Pc-max represents a maximum capillary pressure value,
Pc-min represents a minimum capillary pressure value,
Pc-cut represents a capillary pressure value at which fluid is considered bound,
$T_2$ represents a dimension of the transverse relaxation values,
T2max represents a maximum $T_2$ value, and
T2 min represents a minimum $T_2$ value.

10. A method according to claim 1, wherein:
the at least one parameter indicative of the porous rock sample comprises a parameter indicative of permeability of the porous rock sample.

11. A method according to claim 10, wherein:
the parameter indicative of permeability of the porous rock sample is given as k and is calculated as $$k = c\Phi^4 \left(\frac{FFV}{BFV}\right)^2$$

wherein c is a calibration constant,
$\Phi$ is porosity of the porous rock sample,
FFV is a parameter indicative of free fluid volume in the porous rock sample, and
BFV is a parameter indicative of bound fluid volume in the porous rock sample.

12. A method according to claim 10, wherein:
the parameter indicative of permeability of the porous rock sample is given as $k_{SDR}$ and is calculated as $$k_{SDR} = c\Phi^4 T_{2lm}^2,$$

wherein c is a calibration constant,
$\Phi$ is porosity of the porous rock sample, and
$T_{2lm}$ is a log mean of a distribution of transverse relaxation values.

13. A method according to claim 12, wherein:
$T_{2lm}$ is calculated from a free fluid distribution, which is determined from integration or addition of the probability distribution function of capillary pressure values as a function of transverse relaxation values of the form $$f_{FF}(T_2) = \frac{1}{A} \int_{P_c = Pc\text{-}min}^{P_c = Pc\text{-}cut} f(P_c, T_2) dP_c.$$

where A is the normalization parameter defined as $$A = \int_{T2min}^{T2max} dT_2 \int_{Pc\ min}^{Pc\ max} f(P_c, T_2) dP_c,$$

where $f(P_c, T_2)$ is the probability distribution function of capillary pressure values as a function of transverse relaxation values,
Pc represents a dimension of the capillary pressure values,
Pc-max represents a maximum capillary pressure value,
Pc-min represents a minimum capillary pressure value,
Pc-cut represents a capillary pressure value at which fluid is considered bound,
$T_2$ represents a dimension of the transverse relaxation values,
T2max represents a maximum $T_2$ value, and
T2 min represents a minimum $T_2$ value.

14. A method according to claim 1, further comprising:
generating a pore network model of the porous rock sample based on the probability distribution function of capillary pressure values as a function of NMR property values.

15. A method according to claim 14, wherein:
the pore network model includes a frequency distribution of pore body diameters that are determined using the probability distribution function of capillary pressure values as a function of transverse relaxation values; and
the pore network model includes a frequency distribution of pore throat sizes that are determined using the probability distribution function of capillary pressure values as a function of transverse relaxation values.

16. A method according to claim 1, wherein:
the processing of iv) involves inversion of the NMR data written in a two-dimensional matrix form of $$M = K1 \cdot F \cdot K2^T,$$

where M is a two-dimensional matrix whose rows correspond to a number of echoes in the detected resulting NMR signals and whose columns corresponds to different applied experimental pressure values,
F is a two-dimensional matrix whose rows correspond to different transverse relaxation values and whose columns corresponds to different capillary pressure values,
K1 is a two-dimensional kernel matrix where element (i,j) of K1 is defined to be $$K1_{ij} = \exp\left[-\frac{t_i}{T_{2,j}}\right],$$

where $t_i$ is an i-th value of an echo time t for the echoes over j transverse relaxation values of the F matrix;
$T_2$ represents a dimension of the transverse relaxation values; and
K2 is a two-dimensional kernel matrix defined as:

$$K2_{kl} = S_w(P_{cent,k}, P_{c,l}),$$

where $S_w(P_{cent,k}, P_{c,l})$ is a step function or modified step function representing saturation of the pore sample as a function of applied experimental pressure.

17. A method according to claim 1, wherein:
the processing of iv) involves inversion of the NMR data written in a one-dimensional matrix form of $$m = k \cdot f,$$

where m is a one-dimensional matrix whose i-th element corresponds to the data acquired with the i-th pair of echo time and applied experimental pressure,
f is a one-dimensional matrix whose j-th element corresponds to the j-th pair of transverse relaxation value and capillary pressure value,
k is a one-dimensional kernel matrix defined as $$k_{ij} = S_w(P_{cent,k}, P_{cl})\exp\left[-\frac{t_i}{T_{2,j}}\right]$$

where $S_w(P_{cent,k}, P_{c,l})$ is a step function or modified step function representing saturation of the pore sample as a function of applied experimental pressure,
$T_2$ represents a dimension of the transverse relaxation values, and
$t_i$ is the i-th value of the echo time $t_{echo}$ for the echoes over the j transverse relaxation values of the f matrix.

18. A method according to claim 1, wherein:
the processing of iv) involves inversion of the NMR data for each given capillary pressure values to obtain a distribution of transverse relaxation values for each given capillary pressure value.

19. A method according to claim 18, wherein:
the processing of iv) further involves inversion of the distribution of transverse relaxation values for each given capillary pressure values written in matrix form as $$D = K_D \cdot F,$$

where D is a two-dimensional matrix whose rows correspond to the different transverse relaxation values and whose columns correspond to different applied experimental pressure values,
F is a two-dimensional matrix whose rows correspond to different transverse relaxation values and whose columns corresponds to different capillary pressure values, and
$K_D$ is a two-dimensional kernel matrix defined as $$K_{D,ij} = S_w(P_{cent,i}, P_{c,j})$$

where $S_w(P_{cent,i}, P_{c,j})$ is a step function or modified step function representing saturation of the pore sample as a function of applied experimental pressure.

20. A system for characterizing a porous rock sample, comprising:
a capillary pressure apparatus and an NMR apparatus, wherein the capillary pressure apparatus is configured to subject the porous rock sample to an applied experimental pressure where a first fluid that saturates the porous rock sample is displaced by a second fluid, and the NMR apparatus is configured to apply an NMR pulse sequence to the porous rock sample subsequent to the operations of capillary test apparatus, detect resulting NMR signals from the porous rock sample, and generate and store NMR data representative of the detected resulting NMR signals, wherein the operations of the capillary pressure apparatus and the NMR apparatus are repeated over varying applied experimental pressure to obtain NMR data associated with varying applied experimental pressure values; and
at least one data processor, operable coupled to the NMR apparatus, wherein the at least one data processor is configured to process the NMR data associated with varying applied experimental pressure values to obtain a probability distribution function of capillary pressure values as a function of NMR property values, and to process the probability distribution function of capillary pressure values as a function of NMR property values to determine at least one parameter indicative of the porous rock sample.

\* \* \* \* \*